United States Patent
Kilian et al.

(10) Patent No.: US 9,376,687 B2
(45) Date of Patent: Jun. 28, 2016

(54) ALGAL ELONGASE 6

(71) Applicant: Aurora Algae, Inc., Hayward, CA (US)

(72) Inventors: Oliver Kilian, Alameda, CA (US); Bertrand Vick, Oakland, CA (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 14/328,463

(22) Filed: Jul. 10, 2014

(65) Prior Publication Data

US 2015/0104875 A1   Apr. 16, 2015

Related U.S. Application Data

(63) Continuation of application No. 13/459,215, filed on Apr. 29, 2012, now Pat. No. 8,809,046.

(60) Provisional application No. 61/480,364, filed on Apr. 28, 2011.

(51) Int. Cl.
  *C12N 15/79*   (2006.01)
  *C12N 9/00*   (2006.01)
  *C12N 9/10*   (2006.01)
  *C12N 15/82*   (2006.01)

(52) U.S. Cl.
  CPC .............. *C12N 15/79* (2013.01); *C12N 9/1029* (2013.01); *C12N 9/93* (2013.01); *C12N 15/8247* (2013.01); *C12Y 602/01003* (2013.01)

(58) Field of Classification Search
  None
  See application file for complete search history.

(56) References Cited

U.S. PATENT DOCUMENTS

| | | | |
|---|---|---|---|
| 1,926,780 A | 9/1933 | Lippincott |
| 3,468,057 A | 9/1969 | Buisson et al. |
| 3,962,466 A | 6/1976 | Nakabayashi |
| 4,003,337 A | 1/1977 | Moore |
| 4,267,038 A | 5/1981 | Thompson |
| 4,365,938 A | 12/1982 | Wariner |
| 4,535,060 A | 8/1985 | Comai |
| 4,658,757 A | 4/1987 | Cook |
| 5,105,085 A | 4/1992 | McGuire et al. |
| 5,478,208 A | 12/1995 | Kasai et al. |
| 5,527,456 A | 6/1996 | Jensen |
| 5,661,017 A | 8/1997 | Dunahay et al. |
| 5,668,298 A | 9/1997 | Waldron |
| 5,723,595 A | 3/1998 | Thompson et al. |
| 5,823,781 A | 10/1998 | Hitchcock et al. |
| 6,027,900 A | 2/2000 | Allnutt et al. |
| 6,117,313 A | 9/2000 | Goldman et al. |
| 6,143,562 A | 11/2000 | Trulson et al. |
| 6,166,231 A | 12/2000 | Hoeksema |
| 6,297,054 B1 | 10/2001 | Maliga et al. |
| 6,372,460 B1 | 4/2002 | Gladue et al. |
| 6,448,055 B1 | 9/2002 | Shimizu et al. |
| 6,736,572 B2 | 5/2004 | Geraghty |
| 6,750,048 B2 | 6/2004 | Ruecker et al. |
| 6,831,040 B1 | 12/2004 | Unkefer et al. |
| 6,871,195 B2 | 3/2005 | Ryan et al. |
| 7,244,609 B2 | 7/2007 | Drocourt et al. |
| 7,381,326 B2 | 6/2008 | Haddas |
| 7,410,637 B2 | 8/2008 | Sayre et al. |
| 7,449,568 B2 | 11/2008 | Fukuda et al. |
| 7,547,551 B2 | 6/2009 | Schuler et al. |
| 8,039,230 B2 | 10/2011 | Otte et al. |
| 8,119,859 B2 | 2/2012 | Vick et al. |
| 8,314,228 B2 | 11/2012 | Kilian et al. |
| 8,318,482 B2 | 11/2012 | Vick et al. |
| 8,440,805 B2 | 5/2013 | Kilian et al. |
| 2003/0049720 A1 | 3/2003 | Hoshino |
| 2003/0140021 A1 | 7/2003 | Ryan et al. |
| 2003/0143743 A1 | 7/2003 | Schuler et al. |
| 2003/0199490 A1 | 10/2003 | Antoni-Zimmerman |
| 2003/0211089 A1 | 11/2003 | Sayre et al. |
| 2004/0161364 A1 | 8/2004 | Carlson |
| 2004/0262219 A1 | 12/2004 | Jensen |
| 2005/0064577 A1 | 3/2005 | Berzin |
| 2005/0095569 A1 | 5/2005 | Franklin |
| 2005/0124010 A1 | 6/2005 | Short et al. |
| 2005/0170479 A1 | 8/2005 | Weaver et al. |
| 2005/0181345 A1 | 8/2005 | Bradbury et al. |
| 2005/0260553 A1 | 11/2005 | Berzin |
| 2006/0031087 A1 | 2/2006 | Fox et al. |
| 2006/0044259 A1 | 3/2006 | Hotelling et al. |
| 2006/0045750 A1 | 3/2006 | Stiles |
| 2006/0101535 A1 | 5/2006 | Forster et al. |
| 2006/0122410 A1 | 6/2006 | Fichtali et al. |
| 2006/0155558 A1 | 7/2006 | Corpening |
| 2006/0166243 A1 | 7/2006 | Su et al. |

(Continued)

FOREIGN PATENT DOCUMENTS

| | | |
|---|---|---|
| CN | 1627764 | 6/2005 |
| CN | 1867140 | 11/2006 |

(Continued)

OTHER PUBLICATIONS

Renaud SM et al. Effect of light intensity on the proximate biochemical and fatty acid composition of *isochrysis* sp. and *Nannochloropsis oculata* for use in tropical aquaculture. 1991. Journal of Applied Phycology. 3:43-53.*
In Journal37/2013 A1, IN, Sep. 13, 2013, Vick et al.
In Journal31/2013 A1, IN, Aug. 2, 2013, Kilian et al.
Santin-Montanya, I. "Optimal Growth of Dunaliella Primoiecta in Axenic Conditions to Assay Herbicides," Chemosphere, 66, Elsevier 2006, pp. 1315-1322.
Felix, R. "Use of the cell wall-less alga Dunaliella bioculata in herbicide screening tests," Annals of Applied Biology, 113, 1988, pp. 55-60.
Janssen, M. "Phytosynthetic efficiency of Dunaliella tertiolecta under short light/dark cycles," Enzyme and Microbial Technology, 29, 2001, pp. 298-305.
Saenz, M.E., "Effects of Technical Grade and a Commercial Formulation of Glyphosate on Algal Population Growth," Bulletin of Enviromental Contamination Toxicology, 1997, 59: pp. 638-644.
Christy et al., "Effects of Glyphosate on Growth of Chlorella," Weed Science, vol. 29, Issue 1, Jan. 1981, pp. 5-7.

(Continued)

*Primary Examiner* — Paul Holland
(74) *Attorney, Agent, or Firm* — Kilpatrick Townsend & Stockton LLP

(57) ABSTRACT

Provided herein are exemplary isolated nucleotide sequences encoding polypeptides having elongase activity, which utilize fatty acids as substrates.

6 Claims, 16 Drawing Sheets

(56) References Cited

U.S. PATENT DOCUMENTS

| | | |
|---|---|---|
| 2006/0166343 A1 | 7/2006 | Hankamer et al. |
| 2006/0192690 A1 | 8/2006 | Philipp |
| 2007/0178451 A1 | 8/2007 | Deng et al. |
| 2008/0118964 A1 | 5/2008 | Huntley et al. |
| 2008/0120749 A1 | 5/2008 | Melis et al. |
| 2008/0160591 A1 | 7/2008 | Wilson et al. |
| 2008/0194029 A1 | 8/2008 | Hegemann et al. |
| 2008/0268539 A1 | 10/2008 | Singh et al. |
| 2008/0293132 A1 | 11/2008 | Goldman et al. |
| 2009/0029445 A1 | 1/2009 | Eckelberry et al. |
| 2009/0061493 A1 | 3/2009 | Trimbur et al. |
| 2009/0061928 A1 | 3/2009 | Lee et al. |
| 2009/0148931 A1 | 6/2009 | Wilkerson et al. |
| 2009/0234146 A1 | 9/2009 | Cooney et al. |
| 2009/0317857 A1 | 12/2009 | Vick et al. |
| 2009/0317878 A1 | 12/2009 | Champagne et al. |
| 2009/0317904 A1 | 12/2009 | Vick et al. |
| 2009/0319338 A1 | 12/2009 | Parks et al. |
| 2009/0325270 A1 | 12/2009 | Vick et al. |
| 2010/0022393 A1 | 1/2010 | Vick |
| 2010/0068772 A1 | 3/2010 | Downey |
| 2010/0100520 A1 | 4/2010 | Dargue et al. |
| 2010/0198659 A1 | 8/2010 | Meltzer et al. |
| 2010/0210003 A1 | 8/2010 | King et al. |
| 2010/0210832 A1 | 8/2010 | Kilian et al. |
| 2010/0314324 A1 | 12/2010 | Rice et al. |
| 2010/0323387 A1 | 12/2010 | Bailey et al. |
| 2010/0330643 A1 | 12/2010 | Kilian et al. |
| 2011/0015415 A1 | 1/2011 | Singh et al. |
| 2011/0059495 A1 | 3/2011 | Bailey et al. |
| 2011/0091977 A1 | 4/2011 | Kilian et al. |
| 2012/0107801 A1 | 5/2012 | Kilian et al. |
| 2012/0190115 A1 | 7/2012 | Kilian et al. |
| 2012/0208279 A1 | 8/2012 | Vick et al. |
| 2012/0277418 A1 | 11/2012 | Kilian et al. |
| 2013/0078716 A1 | 3/2013 | Vick et al. |
| 2013/0102040 A1 | 4/2013 | Radakovits et al. |
| 2013/0131330 A1 | 5/2013 | Kilian et al. |
| 2013/0281683 A1 | 10/2013 | Kilian et al. |
| 2013/0289262 A1 | 10/2013 | Kilian et al. |
| 2013/0295665 A1 | 11/2013 | Kilian et al. |

FOREIGN PATENT DOCUMENTS

| | | |
|---|---|---|
| CN | 1956335 | 5/2007 |
| CN | 101289659 | 10/2008 |
| CN | 102164492 A1 | 8/2011 |
| CN | 102858980 A1 | 1/2013 |
| EP | 2297326 A1 | 3/2011 |
| EP | 2491124 A1 | 8/2012 |
| EP | 2297326 A1 | 11/2013 |
| HK | 1175201 A1 | 6/2013 |
| MX | 2011000934 A1 | 7/2011 |
| WO | WO2004106238 A2 | 12/2004 |
| WO | WO2007084078 A1 | 7/2007 |
| WO | WO2008060571 A2 | 5/2008 |
| WO | WO2008060571 A8 | 5/2008 |
| WO | WO2008106803 A1 | 9/2008 |
| WO | WO2009124070 A1 | 10/2009 |
| WO | WO2009149465 A1 | 12/2009 |
| WO | WO2009149470 A1 | 12/2009 |
| WO | WO2010011335 A1 | 1/2010 |
| WO | WO2010147662 A1 | 12/2010 |
| WO | WO2011011463 A2 | 1/2011 |
| WO | WO2011049995 A1 | 4/2011 |
| WO | WO2012149457 A2 | 11/2012 |
| WO | WO2013166065 A1 | 11/2013 |

OTHER PUBLICATIONS

Roessler et al., "Genetic Engineering Approaches for Enhanced Prodution of Biodiesel Fuel from Microalgae," ACS Symposium Series; American Chemical Society, 1994, pp. 255-270.

Endo et al. "Inactivation of Blasticidin S by Bacillus Cereus II. Isolation and Characterization of a Plasmid, pBSR 8, from Bacillus Cereus,"The Journal of Antibiotics 41 (2): 271-2589-2601, 1988.

Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).

Kindle et al. "Stable Nuclear Transformation of Chlamydomonas Using the Chlamydomonas Gene for Nitrate Reductase" The Journal of Cell Biology 109 (6, part 1): 2589-2601, 1989.

Prein et al. "A Novel Strategy for Constructing N-Terminal Chromosomal Fusions to Green Fluorescent Protein in the Yeast Saccharomyces cerevisiae" FEBS Letters 485 (2000) 29-34.

Schiedlmeier et al., "Nuclear Transformation of Volvox Carteri" Proceedings of the National Academy of Sciences USA 91 (11): 5080-5084 (May 1994).

Wendland et al. "PCR-Based Methods Facilitate Targeted Gene Manipulations and Cloning Procedures" Curr.Gen. (2003) 44:115-123.

Molnar et al., "Highly Specific Gene Silencing by Artificial MicroRNAs in the Unicellular Agla Chlamydomonas reinhardtii," Plant Jour. ePub Jan. 17, 2009, vol. 58, No. 1, pp. 157-164 (Abstract Only).

Chen et al., "Conditional Production of a Functional Fish Growth Hormone in the Transgenic Line of Nannochloropsis occulata (Eustigmatophyceae)," J. Phycol. Jun. 2008, vol. 44, No. 3, pp. 768-776.

Nelson et al., "Targeted Disruption of the NIT8 Gene in Chlamydomonas reinhardtii." Mol. Cell. Bio. Oct. 1995, vol. 15, No. 10, pp. 5762-5769.

Kureshy et al., "Effect of Ozone Treatment on Cultures of Nannochloropsis oculata, isochrysis glabana, and Chaetoceros gracilis,"Journal of the World Aquaculture Society, 1999, 30(4), pp. 473-480.

Genbank Accession No. U71602 (Nannochloropsis sp. Violaxanthing-chlorophyll a binding protein precursor (NANVCP) mRNA, 1998.

Sukenik et al. "Characterization of a Gene Encoding the Light-Harvesting Violaxanthin-Chlorophyll Protein of Nannochloropsis Sp. (Eustigmatophyceae),"Journal of Phycology, Jun. 2000; 36(3), pp. 563-570.

Abe et al., AG610981 Musmusculus molossinus DNA, 2004.

Kopczynski et al., C0268749, Drosophila melanogaster eDNA clone EK092604, 2004.

Csogor et al., "Light Distribution in a Novel Photobioreactor—Modelling for Optimization," Journal of Applied Phycology, vol. 13, pp. 325-333, 2001.

Janssen et al., "Enclosed Outdoor Photobioreactors: Light Regime, Photosynhetic Efficiency, Scale-Up, and Future Prospects," Biotechnology and Bioengineering, vol. 81, No. 2, pp. 193-210, Jan. 2003.

Zittelli et al., "Mass Cultivation of Nannochoropsis Sp. In Annular Reactors," Journal of Applied Phycology, vol. 15, pp. 107-113, Mar. 2003.

Strzepek et al., "Photosynthetic Architecture Differs in Coastal and Oceanic Diatoms," Nature, vol. 431, pp. 689-692, Oct. 2004.

Shi et al., "Analysis of Expressed Sequence Tags from the Marine Microalga Nannochloropsis oculata (eustigmatophyceae)," Journal of Phycol, vol. 44, pp. 99-1 02, 2008.

Thiel et al., "Transformation of a Filamentous Cyanobacterium by Electroporation," Journal of Becteriology, Oct. 1989, vol. 171, No. 10, pp. 5743-5746.

Krienitz et al., "Nannochloropsis limnetica (Eustigmatophyceae), a new species of picoplankton from freshwater," Phycologia. 2000, vol. 39, No. 3, Abstract.

Lee et al., "Isolation and Characterization of a Xanthophyll Aberrant Mutant of the Green Alga Nannochloropsis oculata," Marine Biotechnology, 2006, vol. 8, pp. 238-245.

Sukenik et al., "Regulation of Fatty Acid Composition by Irradiance Level in the Eustigmatophyte Nannochloropsis," Journal of Phycol., 1989, vol. 25, pp. 686-692.

Rocha et al., "Growth Aspects of the Marine Microalga Nannochlorpsis gaditana," Biomolecular Engineering, 2003, vol. 20, pp. 237-242.

(56) References Cited

OTHER PUBLICATIONS

MacIntyre et al., "Primary Production By Suspended and Benthic Microalgae in a Turbid Estuary: Time-Scales of Variability in San Antonio Bay, Texas," Marine Ecology Progress Series, 1996, vol. 145, pp. 245-268.
Dunahay et al, "Manipulation of Miroalgal Lipid Production Using Genetic Engineering," Applied Biochemistry and Biotechnology, 1996, vol. 57/58.
Witkowski et al., "Conversion of a B-Ketoacyl Sythase to a Malonyl Decaboxylas by Replacement of the Active-Site Cysteine with Glutamin,"Biochemistry, 1999, val. 38. 11643-11650.
Kisselev, "Polypeptide Release Factors in Prokaryotes and Eukaryotes: Same Function, Different Structure," Structure, vol. 10, Jan. 2002.
Whisstock et al., "Predication of protein function from protein sequence and structure," Q. Rev. Biophysics, 2003, vol. 36, pp. 307-340.
Broun et al., "Catalytic Plasticity of Fatty Acid Modification Enzymes Underlying Chemical Diversity of Plant Lipids," Science, vol. 282, 1998.
Wishart et al., "A Single Mutation Converts a Novel Phosphotyrosine Binding Domain into a Dual-specificity Phosphatase," J. Bioi. Chern. 1995, vol. 270(45), pp. 26782-26785.
Geng et al, "Construction of a System for the Stable Expression of Foreign Genes in Dunaliella Salina," Acta Botanica Sinica 46(3): 342-346, 2004.
Chen et al., "Highly Efficient Expression of Rabbit Neutrophil Peptide-1 gene in Chlorella Ellipsoidea Cells," Current Genetics 39(5-6): 365-370, 2001.
Suga et al., "Control by Osmolarity and Electric Field Strength of Electro-Induced Gene Transfer and Protein Release in Fission Yeast Cells," Journal of Electrostatics 64(12): 796-801, 2006.
International Search Report mailed Sep. 16, 2009 for Application No. PCT/US2009/004296, filed Jul. 24, 2009.
Written Opinion of the International Searching Authority mailed Sep. 16, 2009 for Application No. PCT/US2009/004296, filed Jul. 24, 2009.
Office Action mailed Nov. 14, 2012 in China Patent Application No. 200980138072.X, filed Jul. 24, 2009.
Official Action mailed Jul. 10, 2012 in Mexico Patent Application No. MX/a/20111000934, filed Jul. 24, 2009.
Official Action mailed Mar. 5, 2013 in Mexico Patent Application No. MX/a/2011/000934, filed Jul. 24, 2009.
Duarte et al., "Glyphosate (GP) Effects with Emphasis on Aquatic Organisms," Colunbia Orinoquia, ISSN: 0121-3709, pp. 70-100, 2004.
Technical Card: Glyphosate, Document filed for the Pesticide Action Network and the Alternatives Thereof, for Latin America (RAP-AL)-Communications and Administration Office, Apr. 2008.
Department of Environment, Housing and Territorial Development Ministry, Resolution (1009), published Jun. 17, 2008.
International Search Report and Written Opinion of the International Searching Authority mailed Oct. 30, 2009 for Application No. PCT/US2009/046656, filed Jun. 8, 2009.
International Search Report and Written Opinion of the International Searching Authority mailed Aug. 12, 2009 for Application No. PCT/US2009/003816, filed Jun. 25, 2009.
International Search Report and Written Opinion of the International Searching Authority mailed Dec. 20, 2010 for Application No. PCT/US2010/053265, filed Oct. 19, 2010.
Extended European Search Report mailed Mar. 19, 2013 in European Patent Application 108255513.4, filed on Oct. 19, 2010.
Minoda et al., "Improvement of Culture Conditions and Evidence for Nuclear Transformation by Homologous Recombination in a Red Alga, *Cyanidioschyzon merolae* 10D," Plant and Cell Physiology, vol. 45, No. 6, Jun. 2004, pp. 667-671.
Hallmann et al., "Gene Replacement by Homologous Recombination in the Multicellular Green Alga, *Volvox carteri*," Proceedings of the National Academy of Sciences in the United States of America, vol. 94, No. 14, 1997, pp. 7469-7474.

Kilian et al., "High-efficiency homologous recombination in the oil-producing alga *Nannochloropsis* sp.," Proceedings of the National Academy of Sciences of the United States of America, vol. 108, No. 52, Dec. 2001, pp. 21265-21269.
Extended European Search Report mailed Oct. 19, 2011 in European Patent Application 09759628.2, filed on Jun. 8, 2009.
Hallmann, "Algal Transgenics and Biotechnology," Transgenic Plant Journal, Global Scinece Books Ltd., GB, vol. 1, No. 1, Jan. 2007, pp. 81-98.
International Search Report and Written Opinion of the International Searching Authority mailed Oct. 20, 2010 for Application No. PCT/US2010/001754, filed Jun. 16, 2010.
International Search Report and Written Opinion of the International Searching Authority mailed Sep. 9, 2009 for Application No. PCT/US2009/046650, filed Jun. 8, 2009.
International Search Report and Written Opinion of the International Searching Authority mailed Jun. 15, 2011 for Application No. PCT/US2010/042666, filed Jul. 20, 2010.
Pollock, "High Carbon Dioxide Requiring Mutants of Chlamydomonas Reinhardtil," Created Dec. 2003, [online, retrieved Oct. 14, 2010]<http://etd.lsu.edu/docs/available/etd-0828103-114026/unrestricted/Pollock_dis.pdf>.
Drocourt: GenBank Accession No. X52869.1, created Jan. 3, 1995.
Pan: GenBank Accession No. EE1 09892.1, created Jun. 23, 2008.
Pan: GenBank Accession No. EE1 09907, created Jun. 23, 2008.
Henriquez et al.: GenBank Accession No. Q07CY9, created Oct. 31, 2006.
International Search Report and Written Opinion of the International Searching Authority mailed Oct. 16, 2012 for Application No. PCT/US2012/035633, filed Apr. 27, 2012.
Yu et al., "Construction and characterization of a normalized cDNA library of Nannochloropsis oculata (Eustigmatophyceae)," Chinese Journal of Oceanology and Limnology, vol. 28, No. 4, pp. 802-807, 2010.
Lumbreras et al., "Efficient Foreign Gene Expression in Chlamydomonas Reinhardtii Mediated by an Endogenous Intron," The Plant Journal, vol. 14, No. 4 Jan. 1, 1998, pp. 441-447, XP001150496, ISN: 0960-7412, DOI: 10, 1046/j.1365-313X. 1998. 00 145.X.
Rose A.B., "Intron-Mediated Regulation of Gene Expression," Current Topics in Microbiology and Immunology vol. 326, Jan. 1, 2008, pp. 277-290, XP009145370, ISSN: 0070-217X.
Rose A.B., "The Effect of Intron Location on Intron-Mediated Enhancement of Gene Expression in Arabidopsis," The Plant Journal, vol. 40, No. 5, Dec. 1, 2004, pp. 744-751, XP55029911, ISSN: 0960-7412, DOI:10.1111/j. 1365-313X.2004.02247.
International Search Report and Written Opinion of the International Searching Authority mailed Sep. 13, 2013 in Application No. PCT/US2013/038939 filed Apr. 30, 2013.
Notice on the First Office Action mailed May 20, 2013 in Chinese Application No. 201080058106.7 filed Oct. 19, 2010.
Examination Report mailed Feb. 20, 2013 in Australian Application No. 200927 4500 filed Jul. 24, 2009.
Examination Report mailed Apr. 29, 2013 in European Application No. 09759628.2 filed Jun. 8, 2009.
Examination Report mailed Aug. 29, 2013 in Australian Application No. 2009255947 filed Jun. 8, 2009.
Examination Report mailed Sep. 19, 2013 in Australian Application No. 2010310765 filed Oct. 19, 2010.
Notice on the Second Office Action mailed Sep. 24, 2013 in Chinese Application No. 200980138072.x filed Jul. 24, 2009.
Zuo-Xi Ruan et al., Effects of Acute Glyphosate Exposure on the Growth and Physiology of Nostoc Sphaeroides, an Edible Cyanobacterium of Paddy Rice Fields, Acta Hydrobiologica Sinica, Jul. 2008 vol. 32, No. 4.
Office Action mailed Nov. 11, 2013 in Mexican Application No. MX/a/2011/00934 filed Jul. 24, 2009.
GenBank Acession No. ER498938 GI: 133929743 May 22, 2007.
Second Office Action Mailed Feb. 7, 2014 in Chinese Application No. 201080058106.7 filed Oct. 19, 2010.

* cited by examiner

ATGACTGCCCAGGGCGTGCCCTTTCACCCCATCTGGCAGCTTATCCCGGCCCTGTCGCCCTTCTACACATCCTATGAGAAGCATTTTGATGCCACCGCCTCCTTTATTTTCCT
CTATCGCCACACCTGGGTCCCTCTCCTGGCCACTGCCCTTTACTTCGCCTTTTGCTACTACGGCCCGAAAGCGATGCGTCACCGCAAGGCTTTTGACCTCAAGACCATTCTCT
GCCTTTGGAATCTGTCGTTGTCACTCATAAGTTTTGCGGGCGCCGTCCGTGTGGGTACCCATCTCTTGTACCTGCTGTCCCCGTGGGGCGGATTTTCCTTTCGAGACACGAT
CTGCGAGTCCCCTGAAGCGACTTACGCCGACAACGCCACGGGCCTTTGGTGCGTCGTCTTCACTGTTTCCAAGCTCCTCGAATTAGTCGACACTATATTTGTGGTGTTGCG
GAAGAAGCCTCTCATTTTCCTGCATTGGTACCACCATGCGACTGTCCTTTTGTGCTCATGGTTCGGGCATGTCACGTTCACGCCAGCCCTTTATTTCATGGCAATTAATTACT
CGATTCACGGCGTGATGTACATGTACTTCTTTCTAATGGCAATTAAAAAAGTCCCACAGTGGTTCAATCCTATGTGGCTGACGGTAGCGCAGATCAGCCAAATGTTTGTGG
GCATTTGGGTGATTGTCATGAGTTGTTACTATAAGTATTTCGAGGGCGCTCAGGGAGAAGGAATGGGGAAGGGATGCGCGATTGACGGCCGAATGATTGTGGCGATTT
GTTTAATGTATTCGACGTACCTAGTATTGTTCGTCAAGTTTTTTGTACAACGATATGCGGGCCAACAAAAGCGCAAGGGAGCGAGGGAGGTGGCGGTGGTGGGGAAGG
AGGATAAGGCGACCATGACGGATAGGAAGCGGCATATGGAGCTAAACATCCTTGCTTCGGATCGAGAGGAAGTGAAAGACGAGTTTCGGGTCAAAAAAGAATAA

FIG. 1

```
ATGCCCAAGCTCCCAGAAATCTCTAACATCTTCAAATTCTTGAAGGCAGACCCTTCCAAGATCGTCCCCTACAAGAGCATCCCGGACAAAGTGCCCTTCACACAGGTACG
CGTCACCTTCCTCTTTTTTCTTCTTGCTACATCAGATCATATTTGTACTATCTACGCTGTCTACTATCGAGGAAAGGGCAAATTGTGTGCGTGCTGTGTACAAGTTTCTCTC
TTCTCTTCACAACGTTGTGTCCTCATAATGGTACCCTGCCTGATGATATGGTGCAACACACGGCCTCGCGCAGGCGGGCAGTTTCTGGTCATTAGCGTTGGCGCTCATCG
CCTTCTGATTCTATTGGAATAATAGCTCAATTATATAGCATGCACTGGCTTCCCCTTGAAAATGAGATGCGAATTTCTTTACTGAGTTTTATCCCCTTTACTCTCCCGCACC
TACAGCTCTTTCAGCATTACCCCGTCTTAGACCCCTTGTATACCCAGTATGAGAAGAATTTCTATGCGAGTACTTACGTCAAATTTGCGCAAGACACCTGGCCGGTCCTTC
CCCTTGCCTTGTGCGGAATGTACGCGCTGATGATCATCGTCGGCACTAAAGTCATGGTCTCACGGCCCAAGCACGAGTGGAAGACGGCGTTGGCATGCTGGAACCTGA
TGTTGAGCATTTTCTCCTTCTGTGGGATGATTAGGACGGTTCCGCATTTGCTGCACAATGTGGCGACGTTGCCCTTTAAGGTAGGTACCCCCCTCGATCCTCTCCTCCCTC
CCTTCCTCCCTCACTCCCTCTCTACTATGCCCCCGTCCTGGCCCCTCCGTTGTCGTTTGGCGCTGGGGCCTCCGATAGTTACAGCCACATTCACCTGTAATATTCTCCTATTT
TACTTCTTTTCTCAATTCTCAGGACACGATCTGCCGGCACCCCGCGGAAACGTACGGTGAAGGGGCCTGCGGCATGTGGGTGATGCTCTTCATCTTCAGCAAAGTCCCC
GAGCTAGTAGACACGGTCTTTATCGTCTTTCGCAAAAGCAAGCTGCAGGTATGTATGTATTACTTTTATCTCCTATTGTTTCTGTCTTTCCTTCCCGCCCTCCATTCGTCGT
GTGGATGTAATAGATGAAATTCTTGATCAAGACTTTCCAGAAGGCTCGGAATTGGAGTCGGCCGTGTGTGTGGATGGATACCATAAGAAATTAAAGAGCTCCGTCTCA
TCTCTCCTCCCACCATTCCCCATCCCATTCCGCACCCAACCACTCAGTTCCTGCATTGGTACCACCACATTACCGTCCTCCTCTTCTGCTGGCACTCATACGCCGTCACCTCC
TCCACCGGCCTCTACTTCGTGGCCATGAACTACTCCGTGCATGCCATCATGTACGCCTACTACTACCTGGTACGTGCCTTATTTCTCCCGTCCCTCTATTAGTTTCTTTCCCC
TCACGCTACCGTCTCATACTTTACATATCCTTGTACTCCCACTCATAAGGCTTTTCTTTTCTCCTCTCCCTTCCCCCTTCCCTAATCACCTCCCTTAGACTGCCATTAACGCCT
GGCCTAAGTGGATTCCCCCCTCCATCATCACCGTCGCGCAGATCTCGCAAATGATCGTCGGTGTTGGAATCTGTGCTTCCTCTTTTTACTTCCTGTATACAGACCCAGAGC
ATTGCCAGGTGAAGCGTCAAAATGTATACGCAGGGGCTCTAATGTATGGAAGTTACCTATATCTGTTCTGTGACTTCTTTGTGCGACGTTTTTTGAGAGGAGGCAAGCC
AAGATTGGGAGAGGAGAAGAGTGCGGTGTTGACGATGGCCAAGAAAATCAAGGCTATGTAA
```

FIG. 2

```
ATGACAACGGCCTTCTTCGAGGTGCTGGGCATGTACGTGCCTTCCGAGAACTACACGGAGCGTTTTTACACGGTGCGCGGGAATGAGTTCCACCAAGTCTTCCAAG
GCTTCCCAGCCCTTGCCCCTTTATACATGGACTGGGAGAAGAATTACAATGCGGAGAAGGTCTTTTGGTTCATTATCGACAACTCGTGGATTCCCTGGTTCTCGCTCT
GCGTGTATTTGCTCTTCATCTTCGGCTACCCCGCCCTGGCCAAACGCTACAATATCGGCTACATCTCCGCTCGGACACAGATGGCCTGCTGGAATTTCTTGCTTGCTTC
ATTTAGTTGGATTGGAGCGATGCGGGTGGTACCTCACTTTTTTTTCCTGCTCAAGGACGTGGGCTTTGAAGAGGTAGGGGGGAAGGAGGGAGGGAGGGGAAAA
AGGGAAGGAGGACGATAGGTGGATAGAGTACTATTTTGCTTCTAGTTTGGCAGAAAGGTCAGACACTTAAATCCGGAAGACGAAGAAGCGATAAAATTCTTTTAC
AATGCTAAATTGTTTGACGTCTTGGTCATTCCTTCCCTCCTTCTCCCCTTCCTCCCTCCTCCGCTCCTCCCCAGGTGTTGTGCGGGGCACCGGAGCCGCTGTATGGCGA
CGGTGCTGTCGGATTCTGGATCCAGGCGTTTGTCTTGAGCAAGGTGGCCGAGCTGCTGGATACGGTCTTTGTGGTATTGCGGCAAAAAGACCCGATCTTCTTGCATT
GGTACGTGCCCTCCTTCCCTCCCTTTCCTCCCTCTCCCCCTCCCTCTTTCCTGCACCAACCCACGGCGTTTGCTTGTCGTTGGGTTGCGGGAAAGTCTGAGAATGTCCT
CACATTGGCATGTGGGAGGGGGAAAGAGAGAAAAAGAGAAAGAGATCGACGGAGGGAGGGAAACTGGACCGGCTAAAAGGGACCGGGTAAAGGGGCGGA
GAAACACCAAGGAGAGGTCTTTCTCACTCATTCGTCCCTGCCTATCGACACTCCCCCCCCCGCATTCCCTAGGTACCACCATGTGACCGTGCTGCTCTTCACCTGGTTC
ACGTACTCGAACGAGAACCCGGGGATCATCTTCATCGCCATGAACTACTCGGTGCACGCCGTCATGTACACCTACTACTGGCTCGCCATCGTCAAGCGCGTCCCCGA
CTGGTTCCCCACATGGCTCATCACTCTCGCGCAGATCGCACAGATGGTACGTCTCCCGCTCCCTCTCTGCTTCTCTCCCTCCCTTTCCTGCTCCCCCACACCTTATTTGC
TCAATCGAAGCGCCCTCCTCAGGCGGTGCCGTGCCACGGCAATGTCGAGGACGGTGTCAGTGGGGCGGTGTTAGTCATGTATAGAGCTGTAGGAATACCTTAATG
GCTTCCTTGCTCGGTAGGACTACCCCAAGGGCTCTGTTTGTCGCCTTGGACGCGACAGGGGCTCTGGCCTAGTGACATGTGCTCACCCCTCCTTCCCTCTCTCCCCCC
CTTCCTCCCTCTTTCCCTCCGTCGCCGCCTAGATCGTGGGAGTGTTTGTCGCCTACAACTACTACCGCGTCTTGTCCTCGGGCGGCTCCTGCGCCGTCTCGACGGATCT
GCTGTGGGCATGCGCGTTGATGTACTCGACGTACCTCTACTTGTTTTGTGAGTTTGCTGTCCGCAGGTACATCCTGGGCAGGGGCAACCGGGCAGTGGCGGCGGG
GAAGGGCAAGAAGAAGACCAAGTAG
```

FIG. 3

ATGTCGGCAATGTCACTACCCCCGTGGCTATGGCAAGACCCCACCCCTCTTTACAAAACAAGCCAGTATATCACTCGCGACCCCTTGAACC
CGCGGCGGTTCGTGCAAGTATTTCAATCCATCCCAGTCCTTGAACCGCTCTATACCGAGTTTGAGAAAAAATTTAATGTGAAGGAATCGT
ATCGCATCATCCGGGACAACACCTGGCTGCCCATAATTGCCACCATTCTGTACCTCTCCTTCATGATCGAAGGCCGAAAATACGTGGAACG
CCGGAAGCTTGAGGGCAAAGGACCCGTGAATCTGGGACGATTCCCAGCGTTCTGGAATGCTTTCCTGGCGTCGTTTTCCATTCTAGGTAC
CTTGCGCGTAGTGCCGCATCTGTTGTTCATGTTCACGCATAAGAATTTCAGGGGGACGGTTTGCGAGCCGCCTGATACGGCGGGGTATGG
TGATGGGGCGGCGGGGATGTGGGTGATGCTATTTACGGTTTCCAAGGTCTTTGAATTGGTGGACACGATGATCTTGGTGTTGAAGGGGA
AGAATCCTATGTTTCTGCATTGGTGAGGAAGACGTGTGGGAGGAGGGAGGGAGGGATGGAGGGATGGCGGGCGGGAAAAGCATTCG
AAATATCACCATACTTATTCCACTCGTCGCTCTCTTCGTCCCGACTCTTCACCACAGGTACCACCACGTGACGGTGCTCCTCTACACATGGTT
CTCCTACTCGGCTCGCAATCCCGGCATTTATTTCGTCGCCATGAACTACTCCGTGCACGCCGTCATGTACTCCTACTACTTCCTGACGGAGA
TCAAGCTCTGGCCGAAATGGTTCAAGTATGTGCCCTTCTTTCCCTCTCGCTCTTCCTTACTCCCTCCCTTTCTCCTTCTTCCCTTCATTGCGTCA
TTCATTTCCACAAGGANNNNNNNNNNagCCCTATGTGGATCACCATGGCCCAAATATCGCAGATGCTTGCCGGGGTCGGTATCACCATCG
CCTCGTTCCTCTACGCCCGTGACCCTTCCTGCGGAGTTGTTCGGGATATGATTCCCTGGTGCGCGGGGATGTACGCGACCTACCTGTACTT
CTTCGTCTTGTTTTTCATGGAGCGTTTCTGGCCGTCCATTTTGAATTCATCATCATCATCATCATCATCATCATCATCATCATCGTCATCGTCG
TCGTCATCGTCGTCGTCGTCGTCGTCAAGAAGAAAATGGAAGGAGTTGGGACGGGGGGAGAATAATGAGGCAGGAACAGCTCCG
GCGGCTGGAGGGGTGGGAAGGAGGACAGCCACGAGGGGAGGAAAGTCTAGGAAAGAAGAATAG

FIG. 4

ATGTCATGGTTTTTGGACCCCGCCCCCCTCTACGAGACCAGCGAATATGTCACCCGTGATCCTGTCAACCCCGTCCGCTTTGTGCAAGTGTTCCAATCTATCCCGGCAC
TCGAACCTCTCTACACCGAGTGGGAAAAGAATTTTAACGTCAAGGAGTCCTACCGCATTATTCGAGACAACTGCTGGGTCCCTGTCATTGCCGTCATCCTATATCTATC
CTTCCTAGTCGAAGGCAGGAACTATGTGGAGCGACGAAAGAAAGCAGGCAAAGGACCGGTTAATCTCGGTCGATTCCCGGCAATTTGGAATGGGTTCTTGGCCATC
TTCTCGATACTTGGGGCTTTGCGCGTGGTCCCTCATTTCCTGTTTTTGTTCACACATAAGGATTTTAAGGAGACGGTTTGTGAGGCTCCTGATACGGCGGGGTATGGT
GATGGGGCGGCAGGGATGTGGGTGATGCTGTTTACGGTCTCGAAGGTGTTTGAGTTGATGGATACGGTGATTCTGGTGTTGAAGGGAAAGAACCCAATGTTCTTGC
ACTGGTACGTTGGCGCGGAGTGGCGGACGGAAGAAGGGAAACTGACGATGGACAAAGCGAAAGGTCTCTGTAGCGACATCAAATCCATCTTCCTGTCGCGCACGC
ATGAGGTGCACTCACGCGTGCTTCTGGCACCCCTCTCCCTCCTTTCCTCCCTTTCTTGTCTCTCTTCACCACAGGTACCACCACGTGACAGTGCTCCTCTACACATGGTTC
TCCTACTCGGCCCGCAACCCAGGCCTATACTTTGTCGCCATGAACTACACCGTGCACGCCGTCATGTACTCTTACTACTTCCTGATGGAGATCAAGCTCTGGCCGAAGT
GGCTCAGGTACGTCCCCCTTTCTTCCCCCCCTCTCTCCCTCCCTCCTTCTCTTCCTCCTTTCCTCTCTTCCATCTTCTGTACCGCGCACCCCGCCATCTCACTCCTTCTCTCC
ATCAGAGTCTTCCTTATTATCCACATTAACGCCCTCCTCCCTCTTCCTCTCTTCCCTCCCCCACTCCCTCAGCCCCATTTTCATCACCCTCATGCAAATCTCCCAAATGCTC
GTCGGGGTCGGTATCACGGCCGCCGCCTACATCTTTCAACGCGACCCTTCCTGCGGTGTTGTGCGCGACCTGATCCCCTGGTGTGCCGCCATGTACGCCACCTACCTC
TATTTCTTTGTCGAGTTTTTCGTGGAGCGCTTCTTGGCAGCGTCGAGTACGAAGGCAGGGAAAGAGGAAGGTAAGGGAGGGAAGAGTCAACTGGCGAAAAAGGAT
ATTGGGACCGCGGCCTTCTCGCTGGTGACTGCCAATGGAGCGTCGGTGATGGGGAATGGGAAGAAGGTGGTGTGA

FIG. 5

ATGGCCGCCGCCCTTCTTGCAGACTATCAAAAAACCTGCACGGACTTGTCCGCCGCCATTTTTAAGTGGGCTGACCCTGCGGGCGCCATGGTCAAGGCGCCCACTCG
CACCTGGCCCTTGGCGGGTTTGGACGTGGCCCTGGCTATCGCGGCTTTCTACCTCATCATTGTCTTTGTGGGTTCGGTACGTCTTTGGAATACCGTGTGTATAGAAAG
AGAGATTAGGCGTCGATAAATAGAGTTAGACTGCGTAGGGTATCCAGAGCTGCAACATCTCAGCAGGCGCTTCCACCTCTCTTATCCCCTGTTCTCCACCTATCTTCTA
CCTCCCCTCCCCAAAGGCCATGATGAAGAACGCAAAGCCAGTAAAATTGTACGGCTTGCAATTCTTCTACAACATCTCCCAGGTCGCCCTATGCTCCTATATGTGCATC
GAGGCTGCCATTCAGGCCTACCGTAACGTAGGTCCTCCATCCACCCTTTTCCTCCTTACCATCTCCAATTCCCGCCCCCTCCCTTTGTGTTTTAAGTGAAGAAATACAAA
ATAGCAAAACTTACTTTCGCCTCTGCTAAAATCTAACAGAACTACACCTTCCTCCCTTGCGAGCCGTTCAATGCTACCAACCCACCAATCGCCCCTCTCCTGTGGCTCTT
CTACGTCTCCAAGGTCTTCGACTTCGCCGACACCGTCTTCATCATCCTGGGAAAGAAGTGGAACCAGCTATCATTTCTGCATGTGTACCACCACGTGACCATCTTTTTG
GTGTATTGGTTGAATTTGAATGCGGGATATGATGGCGATATTTTCCTGACAGTCATTCTTAACGGGGCAATCCACACGGTAATGTACACTTACTACTTCCTCTCCATGC
ACACCAAGGACATTTGGTGGAAGAAGTACTTGACACTGTTCCAGATTATTCAGTTCCTGACCATGAATGCTCAGGCGATCTACTTGTTATGTGTGGGTTGCAAGGGGT
TCTCGCCTCAGATTACGAAGCTGTATCTTGGGTACATCCTGTCGCTGTTGGTGCTTTTCCTCAATTTTTACTTCAAATCGTATTCTGGTGTGAAGCCCAATGGTAAGAA
GCCGGTTTCCAAGAAGGCTTAA

FIG. 6

ATGATTGTTTTCCTGCCTCGGATCATGAAAAATCGCCCGGTGAAAGATTTGAGCAAGCCCTTGGCTTTTTGGAATTTCTTCCTAGCAGTGTATAGCACCATCGGGGCC
ATTCGTGTCGTCCCTCACTTGTTGTGGTTTATATCCACGCATACTTTTAAGGAGACTGTCTGTACCGCCCCCTATAGGATCAATGGCGACGGCGCCACTGGTCTGTGG
GTCACGCTCTTCACGCTCTCCAAGGTCGTGGAGTTGGTGGACACCCTCTTTATTTGCTTGAAAGGGAAGAAGCCCATATTCTTGCATTGGTACGTGCTTTAGGTGGGA
AGGGGATACGAGGGACAGGAGCAAGGAATGTGAGAGAAGGCGTAAAAAGACGCACGTGCTCACAATTTTCTTCTCAATGCATATGCATACCTTTCTATTGTCAATA
GGTATCATCATGTTTCCGTCCTCTACTTCACGTGGGCGGCCCACGAGGCTGCCCATGCTGGCATGTATTTCATCGGCATGAACTACACCGTGCACTCGGTTATGTATTC
CTACTACTTCCTCATGGCCATCAAGGCTAAGCCCAAGTGGCTCAAGTAAGTACCTCCCGCCCGTTACTTTTTAATTCCATCTCCCCTCTTTCCTCCCTTTTTCTTCGCTA
ATCGGCAACGCGGACTTGAATCTCGCATCTTGTGCATCCAATCCAGACACCAATTCCTCCCTTCCTCCCTCCCTCAATTCTAGCCCGATCTACATCACCTTCATGCAAAT
TGCGCAAATGATCGTGGGCGTCATCATCACCGCCTTTGGATTTTACTACTCCTCCAAGGATGCTACTTGTGCGGTTGACCCGTTCGTGCTGAAGATCTCGGGAGTAAT
TTATGCGTCTTACCTTTACTTGTTCATGGAGTTTATGATTAAGCGCTTTTTCGTTGGTGGCGGAGGGGTGGCCGGTGGGAAGAAGAAGGGAGGTGCCTCTCCCCGAA
AGGCCAAGGCGAAGAAAGCGCTCTAA

FIG. 7

ATGAAGAACAAGAAGCCCTTTGATCTAAAGTGGCCCTTGGCGTACTGGAACTTGGCTTTGTCCATATTTTCGATCATGGGCGTGATTCGCGTGGTGCCTCACCTT
GTCTACCTGACAGCGACCAAGGGGTTGAGTGTCGTGGCGTGCGGGGCCCCGGAGCCTCTGTATGGCAACGCCGCGGTAGGTTTTTGGGTGCAAGCCTTCATTC
TGTCGAAACTGGCAGAGCTGATCGACACGGTGTTCATCGTTCTGCGGAAGAAGCCTCTACAGTTCTTGCACTGGTACGGGGGTTGGGATGGGGGAATGGTGGA
GCCAAGGAGAGGGAAAGCGAGTTAGCATTCATGCGCTGCTATGTGTCCTTTACCTGGCGCAGAGCGTTTGTGCCCATTACCCATATATAGGGAAAGAAAGGAG
GAAAAAGGACACAGAGGGATCCAAACTGTCCTTATGCAGAGATCAATCGCCACAAGAGGCATGAACCATAGGAAGTCACGCCCTCCTTTTGTTCGCCCCTCCCT
CCTCCTCCCCTTAGGTACCACCACGTGACGGTCCTCCTGTTCACCTGGTTCTGCTACACGAAGGAGAATCCGGGTATCATTTTTGTGGCCATGAATTATTCGGTGC
ATGCCATTATGTATGGCTACTACTTCCTGGTACGTGATCCCTTTCTTTCTCTCTCCTTTCTCCCACTCCTATTGTGCACGCGTGTCTCTACCCCCTGACATAGATCCTT
TTCTCTCTCCCTTCTTCCATGCCTTCATCTCTCTCTTCCTTCTTCTCTACTCTTTCTTCCCGTCCTGTCGCTTCCTCCTTGCTTCGCTCCTGTTATATCCAGGCAACAACT
AAGCCTCTCTTGACACTGACCCACCCTCCCTCCCTCCCGCCCGCCCGACCGCCCTCCTCAGATGGCCATTCAGGTCCGACCTTCCTGGCTGAAGCCAATCTATATC
ACCATGATGCAAATCTCCCAAATGGTGGTGGGCGTCGCCACTGCCGTCTTTTACATCTACAAGATCCGATCGGGCGAGACATGCGCCGTGGATCAGGAACTGCT
TATTGCCTGTGGAGTGATGTACTCTACCTACCTGTATTTGTTCTGTGAGTTTGCGGTAAAGAGGTTCATTTTAGGCGGGCAGGGGGCGGCAGGGGCGCCGAAG
GGAAAAACGAAGGCGCAGTAG

FIG. 8

MTAQGVPFHPIWQLIPALSPFYTSYEKHFDATASFIFLYRHTWVPLLATALYFAFCYYGPKAMRHRKAFD
LKTILCLWNLSLSLISFAGAVRVGTHLLYLLSPWGGFSFRDTICESPEATYADNATGLWCVVFTVSKLLE
LVDTIFVVLRKKPLIFLHWYHHATVLLCSWFGHVTFTPALYFMAINYSIHGVMYMYFFLMAIKKVPQWFN
PMWLTVAQISQMFVGIWVIVMSCYYKYFEGAQGEGMGKGCAIDGRMIVAICLMYSTYLVLFVKFFVQRYA
GQQKRKGAREVAVVGKEDKATMTDRKRHMELNILASDREEVKDEFRVKKE

FIG. 9

MPKLPEISNIFKFLKADPSKIVPYKSIPDKVPFTQLFQHYPVLDPLYTQYEKNFYASTYVKFAQDTWPVL
PLALCGMYALMIIVGTKVMVSRPKHEWKTALACWNLMLSIFSFCGMIRTVPHLLHNVATLPFKDTICRHP
AETYGEGACGMWVMLFIFSKVPELVDTVFIVFRKSKLQFLHWYHHITVLLFCWHSYAVTSSTGLYFVAMN
YSVHAIMYAYYYLTAINAWPKWIPPSIITVAQISQMIVGVGICASSFYFLYTDPEHCQVKRQNVYAGALM
YGSYLYLFCDFFVRRFLRGGKPRLGEEKSAVLTMAKKIKAM

FIG. 10

MTTAFFEVLGMYVPSENYTERFYTVRGNEFHQVFQGFPALAPLYMDWEKNYNAEKVFWFIIDNSWIPWFS
LCVYLLFIFGYPALAKRYNIGYISARTQMACWNFLLASFSWIGAMRVVPHFFFLLKDVGFEEVLCGAPEP
LYGDGAVGFWIQAFVLSKVAELLDTVFVVLRQKDPIFLHWYHHVTVLLFTWFTYSNENPGIIFIAMNYSV
HAVMYTYYWLAIVKRVPDWFPTWLITLAQIAQMIVGVFVAYNYYRVLSSGGSCAVSTDLLWACALMYSTY
LYLFCEFAVRRYILGRGNRAVAAGKGKKKTK

FIG. 11

MSAMSLPPWLWQDPTPLYKTSQYITRDPLNPRRFVQVFQSIPVLEPLYTEFEKKFNVKESYRIIRDNTWL
PIIATILYLSFMIEGRKYVERRKLEGKGPVNLGRFPAFWNAFLASFSILGTLRVVPHLLFMFTHKNFRGT
VCEPPDTAGYGDGAAGMWVMLFTVSKVFELVDTMILVLKGKNPMYHHVTVLLYTWFSYSARNPGIYFVA
MNYSVHAVMYSYYFLTEIKLWPKWFNPMWITMAQISQMLAGVGITIASFLYARDPSCGVVRDMIPWCAG
MYATYLYFFVLFFMERFWPSILNSSSSSSSSSSSSSSSSSSSSSSSSSRRKWKELGRGENNEAGTAPAAGG
VGRRTATRGGKSRKEE

FIG. 12

MSWFLDPAPLYETSEYVTRDPVNPVRFVQVFQSIPALEPLYTEWEKNFNVKESYRIIRDNCWVPVIAVIL
YLSFLVEGRNYVERRKKAGKGPVNLGRFPAIWNGFLAIFSILGALRVVPHFLFLFTHKDFKETVCEAPDT
AGYGDGAAGMWVMLFTVSKVFELMDTVILVLKGKNPMFLHWYHHVTVLLYTWFSYSARNPGLYFVAMNYT
VHAVMYSYYFLMEIKLWPKWLSPIFITLMQISQMLVGVGITAAAYIFQRDPSCGVVRDLIPWCAAMYATY
LYFFVEFFVERFLAASSTKAGKEEGKGGKSQLAKKDIGTAAFSLVTANGASVMGNGKKVV

FIG. 13

MAAALLADYQKTCTDLSAAIFKWADPAGAMVKAPTRTWPLAGLDVALAIAAFYLIIVFVGSAMMKNAKPV
KLYGLQFFYNISQVALCSYMCIEAAIQAYRNNYTFLPCEPFNATNPPIAPLLWLFYVSKVFDFADTVFII
LGKKWNQLSFLHVYHHVTIFLVYWLNLNAGYDGDIFLTVILNGAIHTVMYTYYFLSMHTKDIWWKKYLTL
FQIIQFLTMNAQAIYLLCVGCKGFSPQITKLYLGYILSLLVLFLNFYFKSYSGVKPNGKKPVSKKA

FIG. 14

MIVFLPRIMKNRPVKDLSKPLAFWNFFLAVYSTIGAIRVVPHLLWFISTHTFKETVCTAPYRINGDGATG
LWVTLFTLSKVVELVDTLFICLKGKKPIFLHWYHHVSVLYFTWAAHEAAHAGMYFIGMNYTVHSVMYSYY
FLMAIKAKPKWLNPIYITFMQIAQMIVGVIITAFGFYYSSKDATCAVDPFVLKISGVIYASYLYLFMEFM
IKRFFVGGGGVAGGKKKGGASPRKAKAKKAL

FIG. 15

MKNKKPFDLKWPLAYWNLALSIFSIMGVIRVVPHLVYLTATKGLSVVACGAPEPLYGNAAVGFWVQAFIL
SKLAELIDTVFIVLRKKPLQFLHWYHHVTVLLFTWFCYTKENPGIIFVAMNYSVHAIMYGYYFLMAIQVR
PSWLKPIYITMMQISQMVVGVATAVFYIYKIRSGETCAVDQELLIACGVMYSTYLYLFCEFAVKRFILGG
QGAAGAPKGKTKAQ

FIG. 16

SEQUENCE LISTING

```
<160> NUMBER OF SEQ ID NOS: 16

<210> SEQ ID NO 1
<211> LENGTH: 993
<212> TYPE: DNA
<213> ORGANISM: Nannochloropsis

<400> SEQUENCE: 1
atgactgccc agggcgtgcc ctttcacccc atctggcagc ttatcccggc cctgtcgccc      60
ttctacacat cctatgagaa gcattttgat gccaccgcct cctttatttt cctctatcgc     120
cacacctggg tccctctcct ggccactgcc ctttacttcg ccttttgcta ctacggcccg     180
aaagcgatgc gtcaccgcaa ggcttttgac ctcaagacca ttctctgcct ttggaatctg     240
tcgttgtcac tcataagttt tgcgggcgcc gtccgtgtgg gtaccatct cttgtacctg      300 ctgtccccgt ggggcggatt ttcctttcga gacacgatct gcgagtcccc tgaagcgact     360
tacgccgaca acgccacggg cctttggtgc gtcgtcttca ctgtttccaa gctcctcgaa     420
ttagtcgaca ctatatttgt ggtgttgcgg aagaagcctc tcattttcct gcattggtac     480
caccatgcga ctgtcctttt gtgctcatgg ttcgggcatg tcacgttcac gccagccctt     540
tatttcatgg caattaatta ctcgattcac ggcgtgatgt acatgtactt ctttctaatg     600
gcaattaaaa aagtcccaca gtggttcaat cctatgtggc tgacggtagc gcagatcagc     660
caaatgtttg tgggcatttg ggtgattgtc atgagttgtt actataagta tttcgagggc     720
gctcagggag aaggaatggg gaagggatgc gcgattgacg ccgaatgat tgtggcgatt      780 tgtttaatgt attcgacgta cctagtattg ttcgtcaagt tttttgtaca acgatatgcg     840
ggccaacaaa agcgcaaggg agcgaggag gtggcggtgg tggggaagga ggataaggcg      900
accatgacgg ataggaagcg gcatatggag ctaaacatcc ttgcttcgga tcgagaggaa     960
gtgaaagacg agtttcgggt caaaaaagaa taa                                 993

<210> SEQ ID NO 2
<211> LENGTH: 1837
<212> TYPE: DNA
```

<213> ORGANISM: Nannochloropsis

<400> SEQUENCE: 2

```
atgcccaagc tcccagaaat ctctaacatc ttcaaattct tgaaggcaga cccttccaag      60
atcgtcccct acaagagcat cccggacaaa gtgcccttca cacaggtacg cgtcaccttc     120
ctctttttc ttcttgctac atcagatcat atttgtacta tctacgctgt ctactatcga     180
ggaaagggca aattgtgtgc gtgctgtgta caagtttctc tcttctcttc acaacgttgt     240
gtcctcataa tggtaccctg cctgatgata tggtgcaaca cacggcctcg cgcaggcggg     300
cagtttctgg tcattagcgt tggcgctcat cgccttctga ttctattgga ataatagctc     360
aattatatag catgcactgg cttccccttg aaaatgagat gcgaatttct ttactgagtt     420
ttatcccctt tactctcccg cacctacagc tctttcagca ttacccegtc ttagacccct     480
tgtataccca gtatgagaag aatttctatg cgagtactta cgtcaaattt gcgcaagaca     540
cctggccggt ccttcccctt gccttgtgcg aatgtacgc gctgatgatc atcgtcggca     600
ctaaagtcat ggtctcacgg cccaagcacg agtggaagac ggcgttggca tgctggaacc     660
tgatgttgag cattttctcc ttctgtggga tgattaggac ggttccgcat ttgctgcaca     720
atgtggcgac gttgcccttt aaggtaggta cccccctcga tcctctcctc cctcccttcc     780
tccctcactc cctctctact atgccccgt cctggcccct ccgttgtcgt ttggcgctgg     840
ggcctccgat agttacagcc acattcacct gtaatattct cctatttac ttcttttctc     900
aattctcagg acacgatctg ccggcacccc gcggaaacgt acggtgaagg ggcctgcggc     960
atgtgggtga tgctcttcat cttcagcaaa gtccccgagc tagtagacac ggtctttatc    1020
gtctttcgca aaagcaagct gcaggtatgt atgtattact tttatctcct attgtttctg    1080
tctttccttc ccgccctcca ttcgtcgtgt ggatgtaata atgaaattc ttgatcaaga    1140
cttccagaa ggctcggaat tggagtcggc cgtgtgtgtg atggatacc ataagaaatt    1200
aaagagctcc gtctcatctc tcctcccacc attccccatc ccattccgca cccaaccact    1260
cagttcctgc attggtacca ccacattacc gtcctcctct tctgctggca ctcatacgcc    1320
gtcacctcct ccaccggcct ctacttcgtg ccatgaact actccgtgca tgccatcatg    1380
tacgcctact actacctggt acgtgcctta tttctcccgt ccctctatta gtttctttcc    1440
cctcacgcta ccgtctcata ctttacatat ccttgtactc ccactcataa ggcttttctt    1500
ttctcctctc ccttcccct tccctaatca cctcccttag actgccatta acgcctggcc    1560
taagtggatt ccccccctcca tcatcaccgt cgcgcagatc tcgcaaatga tcgtcggtgt    1620
tggaatctgt gcttcctctt tttacttcct gtatacagac ccagagcatt gccaggtgaa    1680
gcgtcaaaat gtatacgcag gggctctaat gtatggaagt tacctatatc tgttctgtga    1740
cttcttgtg cgacgttttt tgagaggagg caagccaaga ttgggagagg agaagagtgc    1800
ggtgttgacg atggccaaga aaatcaaggc tatgtaa                              1837
```

<210> SEQ ID NO 3
<211> LENGTH: 1736
<212> TYPE: DNA
<213> ORGANISM: Nannochloropsis

<400> SEQUENCE: 3

```
atgacaacgg ccttcttcga ggtgctgggc atgtacgtgc cttccgagaa ctacacggag      60
cgttttaca cggtgcgcgg gaatgagttc accaagtct tccaaggctt cccagccctt     120
gccccttat acatggactg ggagaagaat tacaatgcgg agaaggtctt tggttcatt     180
```

-continued

```
atcgacaact cgtggattcc ctggttctcg ctctgcgtgt atttgctctt catcttcggc    240 tacccccgccc tggccaaacg ctacaatatc ggctacatct ccgctcggac acagatggcc    300
tgctggaatt tcttgcttgc ttcatttagt tggattggag cgatgcgggt ggtacctcac    360
ttttttttcc tgctcaagga cgtgggcttt gaagaggtag gggggaagg agggagggag    420 gggaaaaagg gaaggaggac gataggtgga tagagtacta ttttgcttct agtttggcag    480
aaaggtcaga cacttaaatc cggaagacga agaagcgata aaattctttt acaatgctaa    540
attgtttgac gtcttggtca ttccttccct ccttctcccc ttcctccctc ctccgctcct    600
ccccaggtgt tgtgcgggc accggagccg ctgtatggcg acggtgctgt cggattctgg    660
atccaggcgt ttgtcttgag caaggtggcc gagctgctgg atacggtctt tgtggtattg    720
cggcaaaaag acccgatctt cttgcattgg tacgtgccct ccttccctcc ctttcctccc    780 tctcccctc cctctttcct gcaccaaccc acggcgtttg cttgtcgttg ggttgcggga    840
aagtctgaga atgtcctcac attggcatgt gggagggggg aaagagagaa aaagagaaag    900
agatcgacgg agggagggaa actggaccgg ctaaaggga ccgggtaaag ggggcggaga    960
aacaccaagg agaggtcttt ctcactcatt cgtccctgcc tatcgacact ccccccccg    1020 cattccctag gtaccaccat gtgaccgtgc tgctcttcac ctggttcacg tactcgaacg    1080
agaacccggg gatcatcttc atcgccatga actactcggt gcacgccgtc atgtacacct    1140
actactggct cgccatcgtc aagcgcgtcc ccgactggtt ccccacatgg ctcatcactc    1200
tcgcgcagat cgcacagatg gtacgtctcc cgctccctct ctgcttctct ccctcccttt    1260
cctgctcccc cacaccttat tgctcaatc gaagcgccct cctcaggcgg tgccgtgcca    1320
cggcaatgtc gaggacggtg tcagtggggc ggtgttagtc atgtatagag ctgtaggaat    1380
accttaatgg cttccttgct cggtaggact accccaaggg ctctgtttgt cgccttggac    1440
gcgacagggg ctctgccta gtgacatgtg ctcacccctc cttccctctc tccccccctt    1500
cctccctctt tccctccgtc gccgcctaga tcgtgggagt gtttgtcgcc tacaactact    1560
accgcgtctt gtcctcgggc ggctcctgcg ccgtctcgac ggatctgctg tgggcatgcg    1620
cgttgatgta ctcgacgtac ctctacttgt tttgtgagtt tgctgtccgc aggtacatcc    1680
tgggcagggg caaccgggca gtggcggcgg ggaagggcaa gaagaagacc aagtag       1736
```

<210> SEQ ID NO 4
<211> LENGTH: 1331
<212> TYPE: DNA
<213> ORGANISM: Nannochloropsis
<220> FEATURE:
<221> NAME/KEY: misc_feature
<222> LOCATION: (924)..(932)
<223> OTHER INFORMATION: n is a, c, g, or t

<400> SEQUENCE: 4

```
atgtcggcaa tgtcactacc cccgtggcta tggcaagacc ccacccctct ttacaaaaca     60
agccagtata tcactcgcga ccccttgaac ccgcggcggt tcgtgcaagt atttcaatcc    120
atcccagtcc ttgaaccgct ctataccgag tttgagaaaa aatttaatgt gaaggaatcg    180
tatcgcatca tccgggacaa cacctggctg cccataattg ccaccattct gtacctctcc    240
ttcatgatcg aaggccgaaa atacgtggaa cgccggaagc ttgagggcaa aggacccgtg    300
aatctgggac gattcccagc gttctggaat gctttcctgg cgtcgttttc cattctaggt    360
accttgcgcg tagtgccgca tctgttgttc atgttcacgc ataagaattt caggggacg    420
```

```
gtttgcgagc cgcctgatac ggcggggtat ggtgatgggg cggcggggat gtgggtgatg      480
ctatttacgg tttccaaggt ctttgaattg gtggacacga tgatcttggt gttgaagggg      540
aagaatccta tgtttctgca ttggtgagga agacgtgtgg gaggagggag ggagggatgg      600
agggatggcg ggcgggaaaa gcattcgaaa tatcaccata cttattccac tcgtcgctct      660
cttcgtcccg actcttcacc acaggtacca ccacgtgacg gtgctcctct acacatggtt      720
ctcctactcg gctcgcaatc ccggcattta tttcgtcgcc atgaactact ccgtgcacgc      780
cgtcatgtac tcctactact tcctgacgga gatcaagctc tggccgaaat ggttcaagta      840
tgtgcccttc tttccctctc gctcttcctt actccctccc tttctccttc ttcccttcat      900
tgcgtcattc atttccacaa ggannnnnnn nnagccctat gtggatcacc atggcccaaa      960
tatcgcagat gcttgccggg gtcggtatca ccatcgcctc gttcctctac gcccgtgacc     1020
cttcctgcgg agttgttcgg gatatgattc cctggtgcgc ggggatgtac gcgacctacc     1080
tgtacttctt cgtcttgttt ttcatggagc gtttctggcc gtccattttg aattcatcat     1140
catcatcatc atcatcatca tcatcatcat cgtcatcgtc gtcgtcatcg tcgtcgtcgt     1200
cgtcgtcgtc aagaagaaaa tggaaggagt tgggacgggg ggagaataat gaggcaggaa     1260
cagctccggc ggctggaggg gtgggaagga ggacagccac gaggggagga aagtctagga     1320
aagaagaata g                                                          1331

<210> SEQ ID NO 5
<211> LENGTH: 1376
<212> TYPE: DNA
<213> ORGANISM: Nannochloropsis

<400> SEQUENCE: 5
atgtcatggt ttttggaccc cgcccccctc tacgagacca gcgaatatgt cacccgtgat       60
cctgtcaacc ccgtccgctt tgtgcaagtg ttccaatcta tcccggcact cgaacctctc      120
tacaccgagt gggaaaagaa ttttaacgtc aaggagtcct accgcattat tcgagacaac      180
tgctgggtcc ctgtcattgc cgtcatccta tatctatcct tcctagtcga aggcaggaac      240
tatgtggagc gacgaaagaa agcaggcaaa ggaccggtta atctcggtcg attcccggca      300
atttggaatg ggttcttggc catcttctcg atacttgggg ctttgcgcgt ggtccctcat      360
ttcctgtttt tgttcacaca taaggatttt aaggagacgg tttgtgaggc tcctgatacg      420
gcggggtatg gtgatggggc ggcagggatg tgggtgatgc tgtttacggt ctcgaaggtg      480
tttgagttga tggatacggt gattctggtg ttgaagggaa agaacccaat gttcttgcac      540
tggtacgttg gcgcggagtg gcggacggaa gaagggaaac tgacgatgga caaagcgaaa      600
ggtctctgta gcgacatcaa atccatcttc ctgtcgcgca cgcatgaggt gcactcacgc      660
gtgcttctgg caccctctc cctcctttcc tccctttctt gtctctcttc accacaggta      720
ccaccacgtg acagtgctcc tctacacatg gttctcctac tcggcccgca acccaggcct      780
atactttgtc gccatgaact acaccgtgca cgccgtcatg tactcttact acttcctgat      840
ggagatcaag ctctggccga agtggctcag gtacgtcccc cttcttccc cccctctctc      900
cctccctcct tctcttcctc ctttcctctc ttccatcttc tgtaccgcgc accccgccat      960
ctcactcctt ctctccatca gagtcttcct tattatccac attaacgccc tcctccctct     1020
tcctctcttc cctccccac tccctcagcc ccattttcat caccctcatg caaatctccc     1080
aaatgctcgt cggggtcggt atcacggccg ccgcctacac ctttcaacgc gacccttcct     1140
gcggtgttgt gcgcgacctg atcccctggt gtgccgccat gtacgccacc tacctctatt     1200
```

| | | | |
|---|---|---|---|
| tctttgtcga | gtttttcgtg | gagcgcttct tggcagcgtc gagtacgaag gcagggaaag | 1260 |
| aggaaggtaa | gggagggaag | agtcaactgg cgaaaaagga tattgggacc gcggccttct | 1320 |
| cgctggtgac | tgccaatgga | gcgtcggtga tggggaatgg gaagaaggtg gtgtga | 1376 |

<210> SEQ ID NO 6
<211> LENGTH: 1110
<212> TYPE: DNA
<213> ORGANISM: Nannochloropsis

<400> SEQUENCE: 6

| | | | |
|---|---|---|---|
| atggccgccg | cccttcttgc | agactatcaa aaaacctgca cggacttgtc cgccgccatt | 60 |
| tttaagtggg | ctgaccctgc | gggcgccatg gtcaaggcgc ccactcgcac ctggcccttg | 120 |
| gcgggtttgg | acgtggccct | ggctatcgcg gctttctacc tcatcattgt ctttgtgggt | 180 |
| tcggtacgtc | tttggaatac | cgtgtgtata gaaagagaga ttaggcgtcg ataaatagag | 240 |
| ttagactgcg | tagggtatcc | agagctgcaa catctcagca ggcgcttcca cctctcttat | 300 |
| cccctgttct | ccacctatct | tctacctccc ctccccaaag gccatgatga agaacgcaaa | 360 |
| gccagtaaaa | ttgtacggct | tgcaattctt ctacaacatc tcccaggtcg ccctatgctc | 420 |
| ctatatgtgc | atcgaggctg | ccattcaggc ctaccgtaac gtaggtcctc catccaccct | 480 |
| tttcctcctt | accatctcca | attcccgccc cctcccttg tgttttaagt gaagaaatac | 540 |
| aaaatagcaa | aacttacttt | cgcctctgct aaaatctaac agaactacac cttcctccct | 600 |
| tgcgagccgt | tcaatgctac | caacccacca atcgccctc cctgtggct cttctacgtc | 660 |
| tccaaggtct | tcgacttcgc | cgacaccgtc ttcatcatcc tgggaaagaa gtggaaccag | 720 |
| ctatcatttc | tgcatgtgta | ccaccacgtg accatctttt tggtgtattg gttgaatttg | 780 |
| aatgcgggat | atgatggcga | tattttcctg acagtcattc ttaacggggc aatccacacg | 840 |
| gtaatgtaca | cttactactt | cctctccatg cacaccaagg acatttggtg gaagaagtac | 900 |
| ttgacactgt | tccagattat | tcagttcctg accatgaatg ctcaggcgat ctacttgtta | 960 |
| tgtgtgggtt | gcaagggtt | ctcgcctcag attacgaagc tgtatcttgg gtacatcctg | 1020 |
| tcgctgttgg | tgcttttcct | caattttac ttcaaatcgt attctggtgt gaagcccaat | 1080 |
| ggtaagaagc | cggttccaa | gaaggcttaa | 1110 |

<210> SEQ ID NO 7
<211> LENGTH: 1002
<212> TYPE: DNA
<213> ORGANISM: Nannochloropsis

<400> SEQUENCE: 7

| | | | |
|---|---|---|---|
| atgattgttt | tcctgcctcg | gatcatgaaa aatcgcccgg tgaaagattt gagcaagccc | 60 |
| ttggcttttt | ggaatttctt | cctagcagtg tatagcacca tcggggccat tcgtgtcgtc | 120 |
| cctcacttgt | tgtggtttat | atccacgcat acttttaagg agactgtctg taccgccccc | 180 |
| tataggatca | atggcgacgg | cgccactggt ctgtgggtca cgctcttcac gctctccaag | 240 |
| gtcgtggagt | tggtggacac | cctctttatt tgcttgaaag ggaagaagcc catattcttg | 300 |
| cattggtacg | tgctttaggt | gggaagggga tacgagggac aggagcaagg aatgtgagag | 360 |
| aaggcgtaaa | aagacgcacg | tgctcacaat tttcttctca atgcatatgc ataccttttct | 420 |
| attgtcaata | ggtatcatca | tgtttccgtc ctctacttca cgtgggcggc ccacgaggct | 480 |
| gcccatgctg | gcatgtattt | catcggcatg aactacaccg tgcactcggt tatgtattcc | 540 |

```
tactacttcc tcatggccat caaggctaag cccaagtggc tcaagtaagt acctcccgcc      600
cgttactttt ttaattccat ctcccctctt tcctccctt ttctttcgct aatcggcaac      660
gcggacttga atctcgcatc ttgtgcatcc aatccagaca ccaattcctc ccttcctccc      720
tccctcaatt ctagcccgat ctacatcacc ttcatgcaaa ttgcgcaaat gatcgtgggc      780
gtcatcatca ccgcctttgg attttactac tcctccaagg atgctacttg tgcggttgac      840
ccgttcgtgc tgaagatctc gggagtaatt tatgcgtctt acctttactt gttcatggag      900
tttatgatta agcgcttttt cgttggtggc ggaggggtgg ccggtgggaa gaagaaggga      960
ggtgcctctc cccgaaaggc caaggcgaag aaagcgctct aa                       1002
```

```
<210> SEQ ID NO 8
<211> LENGTH: 1178
<212> TYPE: DNA
<213> ORGANISM: Nannochloropsis

<400> SEQUENCE: 8
atgaagaaca agaagccctt tgatctaaag tggcccttgg cgtactggaa cttggctttg       60
tccatatttt cgatcatggg cgtgattcgc gtggtgcctc accttgtcta cctgacagcg      120
accaaggggt tgagtgtcgt ggcgtgcggg cccccggagc tctgtatgg caacgccgcg      180 gtaggttttt gggtgcaagc cttcattctg tcgaaactgg cagagctgat cgacacggtg      240
ttcatcgttc tgcggaagaa gcctctacag ttcttgcact ggtacggggg ttgggatggg      300
ggaatggtgg agccaaggag agggaaagcg agttagcatt catgcgctgc tatgtgtcct      360
ttacctggcg cagagcgttt gtgcccatta cccatatata gggaagaaa ggaggaaaaa      420 ggacacagag ggatccaaac tgtccttatg cagagatcaa tcgccacaag aggcatgaac      480 catagggaagt cacgccctcc tttgttcgc cctcctcc tcctccctt aggtaccacc      540 acgtgacggt cctcctgttc acctggttct gctacacgaa ggagaatccg ggatcatttt      600
ttgtggccat gaattattcg gtgcatgcca ttatgtatgg ctactacttc ctggtacgtg      660
atccctttct ttctctctcc tttctcccac tcctattgtg cacgcgtgtc tctaccccct      720
gacatagatc cttttctctc tcccttcttc catgccttca tctctctctt ccttcttctc      780
tactctttct tcccgtcctg tcgcttcctc cttgcttcgc tcctgttata tccaggcaac      840
aactaagcct ctcttgacac tgacccaccc tccctccctc ccgcccgccc gaccgccctc      900
ctcagatggc cattcaggtc cgaccttcct ggctgaagcc aatctatatc accatgatgc      960
aaatctccca aatggtggtg ggcgtcgcca ctgccgtctt ttacatctac aagatccgat    1020
cgggcgagac atgcgccgtg gatcaggaac tgcttattgc ctgtggagtg atgtactcta    1080
cctacctgta tttgttctgt gagtttgcgg taaagaggtt cattttaggc gggcaggggg    1140
cggcaggggc gccaaggga aaaacgaagg cgcagtag                            1178
```

```
<210> SEQ ID NO 9
<211> LENGTH: 330
<212> TYPE: PRT
<213> ORGANISM: Nannochloropsis

<400> SEQUENCE: 9

Met Thr Ala Gln Gly Val Pro Phe His Pro Ile Trp Gln Leu Ile Pro
1               5                   10                  15

Ala Leu Ser Pro Phe Tyr Thr Ser Tyr Glu Lys His Phe Asp Ala Thr
            20                  25                  30

Ala Ser Phe Ile Phe Leu Tyr Arg His Thr Trp Val Pro Leu Leu Ala
```

```
                35                  40                  45
Thr Ala Leu Tyr Phe Ala Phe Cys Tyr Tyr Gly Pro Lys Ala Met Arg
             50                  55                  60

His Arg Lys Ala Phe Asp Leu Lys Thr Ile Leu Cys Leu Trp Asn Leu
 65                  70                  75                  80

Ser Leu Ser Leu Ile Ser Phe Ala Gly Ala Val Arg Val Gly Thr His
                 85                  90                  95

Leu Leu Tyr Leu Leu Ser Pro Trp Gly Gly Phe Ser Phe Arg Asp Thr
                100                 105                 110

Ile Cys Glu Ser Pro Glu Ala Thr Tyr Ala Asp Asn Ala Thr Gly Leu
            115                 120                 125

Trp Cys Val Val Phe Thr Val Ser Lys Leu Leu Glu Leu Val Asp Thr
130                 135                 140

Ile Phe Val Val Leu Arg Lys Lys Pro Leu Ile Phe Leu His Trp Tyr
145                 150                 155                 160

His His Ala Thr Val Leu Leu Cys Ser Trp Phe Gly His Val Thr Phe
                165                 170                 175

Thr Pro Ala Leu Tyr Phe Met Ala Ile Asn Tyr Ser Ile His Gly Val
            180                 185                 190

Met Tyr Met Tyr Phe Phe Leu Met Ala Ile Lys Lys Val Pro Gln Trp
        195                 200                 205

Phe Asn Pro Met Trp Leu Thr Val Ala Gln Ile Ser Gln Met Phe Val
210                 215                 220

Gly Ile Trp Val Ile Val Met Ser Cys Tyr Tyr Lys Tyr Phe Glu Gly
225                 230                 235                 240

Ala Gln Gly Glu Gly Met Gly Lys Gly Cys Ala Ile Asp Gly Arg Met
                245                 250                 255

Ile Val Ala Ile Cys Leu Met Tyr Ser Thr Tyr Leu Val Leu Phe Val
            260                 265                 270

Lys Phe Phe Val Gln Arg Tyr Ala Gly Gln Gln Lys Arg Lys Gly Ala
        275                 280                 285

Arg Glu Val Ala Val Val Gly Lys Glu Asp Lys Ala Thr Met Thr Asp
290                 295                 300

Arg Lys Arg His Met Glu Leu Asn Ile Leu Ala Ser Asp Arg Glu Glu
305                 310                 315                 320

Val Lys Asp Glu Phe Arg Val Lys Lys Glu
                325                 330

<210> SEQ ID NO 10
<211> LENGTH: 321
<212> TYPE: PRT
<213> ORGANISM: Nannochloropsis

<400> SEQUENCE: 10

Met Pro Lys Leu Pro Glu Ile Ser Asn Ile Phe Lys Phe Leu Lys Ala
 1               5                  10                  15

Asp Pro Ser Lys Ile Val Pro Tyr Lys Ser Ile Pro Asp Lys Val Pro
             20                  25                  30

Phe Thr Gln Leu Phe Gln His Tyr Pro Val Leu Asp Pro Leu Tyr Thr
         35                  40                  45

Gln Tyr Glu Lys Asn Phe Tyr Ala Ser Thr Tyr Val Lys Phe Ala Gln
     50                  55                  60

Asp Thr Trp Pro Val Leu Pro Leu Ala Leu Cys Gly Met Tyr Ala Leu
 65                  70                  75                  80
```

```
Met Ile Ile Val Gly Thr Lys Val Met Val Ser Arg Pro Lys His Glu
                85                  90                  95

Trp Lys Thr Ala Leu Ala Cys Trp Asn Leu Met Leu Ser Ile Phe Ser
            100                 105                 110

Phe Cys Gly Met Ile Arg Thr Val Pro His Leu Leu His Asn Val Ala
        115                 120                 125

Thr Leu Pro Phe Lys Asp Thr Ile Cys Arg His Pro Ala Glu Thr Tyr
    130                 135                 140

Gly Glu Gly Ala Cys Gly Met Trp Val Met Leu Phe Ile Phe Ser Lys
145                 150                 155                 160

Val Pro Glu Leu Val Asp Thr Val Phe Ile Val Phe Arg Lys Ser Lys
                165                 170                 175

Leu Gln Phe Leu His Trp Tyr His Ile Thr Val Leu Leu Phe Cys
            180                 185                 190

Trp His Ser Tyr Ala Val Thr Ser Ser Thr Gly Leu Tyr Phe Val Ala
        195                 200                 205

Met Asn Tyr Ser Val His Ala Ile Met Tyr Ala Tyr Tyr Leu Thr
    210                 215                 220

Ala Ile Asn Ala Trp Pro Lys Trp Ile Pro Pro Ser Ile Ile Thr Val
225                 230                 235                 240

Ala Gln Ile Ser Gln Met Ile Val Gly Val Gly Ile Cys Ala Ser Ser
                245                 250                 255

Phe Tyr Phe Leu Tyr Thr Asp Pro Glu His Cys Gln Val Lys Arg Gln
            260                 265                 270

Asn Val Tyr Ala Gly Ala Leu Met Tyr Gly Ser Tyr Leu Tyr Leu Phe
        275                 280                 285

Cys Asp Phe Phe Val Arg Arg Phe Leu Arg Gly Gly Lys Pro Arg Leu
    290                 295                 300

Gly Glu Glu Lys Ser Ala Val Leu Thr Met Ala Lys Lys Ile Lys Ala
305                 310                 315                 320

Met

<210> SEQ ID NO 11
<211> LENGTH: 311
<212> TYPE: PRT
<213> ORGANISM: Nannochloropsis

<400> SEQUENCE: 11

Met Thr Thr Ala Phe Phe Glu Val Leu Gly Met Tyr Val Pro Ser Glu
1               5                   10                  15

Asn Tyr Thr Glu Arg Phe Tyr Thr Val Arg Gly Asn Glu Phe His Gln
            20                  25                  30

Val Phe Gln Gly Phe Pro Ala Leu Ala Pro Leu Tyr Met Asp Trp Glu
        35                  40                  45

Lys Asn Tyr Asn Ala Glu Lys Val Phe Trp Phe Ile Ile Asp Asn Ser
    50                  55                  60

Trp Ile Pro Trp Phe Ser Leu Cys Val Tyr Leu Leu Phe Ile Phe Gly
65                  70                  75                  80

Tyr Pro Ala Leu Ala Lys Arg Tyr Asn Ile Gly Tyr Ile Ser Ala Arg
                85                  90                  95

Thr Gln Met Ala Cys Trp Asn Phe Leu Leu Ala Ser Phe Ser Trp Ile
            100                 105                 110

Gly Ala Met Arg Val Val Pro His Phe Phe Leu Leu Lys Asp Val
        115                 120                 125
```

```
Gly Phe Glu Glu Val Leu Cys Gly Ala Pro Glu Pro Leu Tyr Gly Asp
130                 135                 140

Gly Ala Val Gly Phe Trp Ile Gln Ala Phe Val Leu Ser Lys Val Ala
145                 150                 155                 160

Glu Leu Leu Asp Thr Val Phe Val Val Leu Arg Gln Lys Asp Pro Ile
                165                 170                 175

Phe Leu His Trp Tyr His His Val Thr Val Leu Leu Phe Thr Trp Phe
                180                 185                 190

Thr Tyr Ser Asn Glu Asn Pro Gly Ile Ile Phe Ile Ala Met Asn Tyr
                195                 200                 205

Ser Val His Ala Val Met Tyr Thr Tyr Tyr Trp Leu Ala Ile Val Lys
                210                 215                 220

Arg Val Pro Asp Trp Phe Pro Thr Trp Leu Ile Thr Leu Ala Gln Ile
225                 230                 235                 240

Ala Gln Met Ile Val Gly Val Phe Val Ala Tyr Asn Tyr Tyr Arg Val
                245                 250                 255

Leu Ser Ser Gly Gly Ser Cys Ala Val Ser Thr Asp Leu Leu Trp Ala
                260                 265                 270

Cys Ala Leu Met Tyr Ser Thr Tyr Leu Tyr Leu Phe Cys Glu Phe Ala
                275                 280                 285

Val Arg Arg Tyr Ile Leu Gly Arg Gly Asn Arg Ala Val Ala Ala Gly
                290                 295                 300

Lys Gly Lys Lys Lys Thr Lys
305                 310

<210> SEQ ID NO 12
<211> LENGTH: 366
<212> TYPE: PRT
<213> ORGANISM: Nannochloropsis

<400> SEQUENCE: 12

Met Ser Ala Met Ser Leu Pro Pro Trp Leu Trp Gln Asp Pro Thr Pro
1               5                   10                  15

Leu Tyr Lys Thr Ser Gln Tyr Ile Thr Arg Asp Pro Leu Asn Pro Arg
                20                  25                  30

Arg Phe Val Gln Val Phe Gln Ser Ile Pro Val Leu Glu Pro Leu Tyr
                35                  40                  45

Thr Glu Phe Glu Lys Lys Phe Asn Val Lys Glu Ser Tyr Arg Ile Ile
50                  55                  60

Arg Asp Asn Thr Trp Leu Pro Ile Ile Ala Thr Ile Leu Tyr Leu Ser
65                  70                  75                  80

Phe Met Ile Glu Gly Arg Lys Tyr Val Glu Arg Arg Lys Leu Glu Gly
                85                  90                  95

Lys Gly Pro Val Asn Leu Gly Arg Phe Pro Ala Phe Trp Asn Ala Phe
                100                 105                 110

Leu Ala Ser Phe Ser Ile Leu Gly Thr Leu Arg Val Val Pro His Leu
                115                 120                 125

Leu Phe Met Phe Thr His Lys Asn Phe Arg Gly Thr Val Cys Glu Pro
130                 135                 140

Pro Asp Thr Ala Gly Tyr Gly Asp Gly Ala Ala Gly Met Trp Val Met
145                 150                 155                 160

Leu Phe Thr Val Ser Lys Val Phe Glu Leu Val Asp Thr Met Ile Leu
                165                 170                 175

Val Leu Lys Gly Lys Asn Pro Met Tyr His His Val Thr Val Leu Leu
                180                 185                 190
```

Tyr Thr Trp Phe Ser Tyr Ser Ala Arg Asn Pro Gly Ile Tyr Phe Val
            195                 200                 205

Ala Met Asn Tyr Ser Val His Ala Val Met Tyr Ser Tyr Tyr Phe Leu
        210                 215                 220

Thr Glu Ile Lys Leu Trp Pro Lys Trp Phe Asn Pro Met Trp Ile Thr
225                 230                 235                 240

Met Ala Gln Ile Ser Gln Met Leu Ala Gly Val Gly Ile Thr Ile Ala
                    245                 250                 255

Ser Phe Leu Tyr Ala Arg Asp Pro Ser Cys Gly Val Val Arg Asp Met
                260                 265                 270

Ile Pro Trp Cys Ala Gly Met Tyr Ala Thr Tyr Leu Tyr Phe Phe Val
            275                 280                 285

Leu Phe Phe Met Glu Arg Phe Trp Pro Ser Ile Leu Asn Ser Ser Ser
        290                 295                 300

Ser Ser Ser Ser Ser Ser Ser Ser Ser Ser Ser Ser Ser Ser Ser Ser
305                 310                 315                 320

Ser Ser Ser Ser Ser Ser Arg Arg Lys Trp Lys Glu Leu Gly Arg
                    325                 330                 335

Gly Glu Asn Asn Glu Ala Gly Thr Ala Pro Ala Ala Gly Gly Val Gly
                340                 345                 350

Arg Arg Thr Ala Thr Arg Gly Gly Lys Ser Arg Lys Glu Glu
            355                 360                 365

<210> SEQ ID NO 13
<211> LENGTH: 340
<212> TYPE: PRT
<213> ORGANISM: Nannochloropsis

<400> SEQUENCE: 13

Met Ser Trp Phe Leu Asp Pro Ala Pro Leu Tyr Glu Thr Ser Glu Tyr
1               5                   10                  15

Val Thr Arg Asp Pro Val Asn Pro Val Arg Phe Val Gln Val Phe Gln
            20                  25                  30

Ser Ile Pro Ala Leu Glu Pro Leu Tyr Thr Glu Trp Glu Lys Asn Phe
        35                  40                  45

Asn Val Lys Glu Ser Tyr Arg Ile Ile Arg Asp Asn Cys Trp Val Pro
    50                  55                  60

Val Ile Ala Val Ile Leu Tyr Leu Ser Phe Leu Val Glu Gly Arg Asn
65                  70                  75                  80

Tyr Val Glu Arg Arg Lys Lys Ala Gly Lys Gly Pro Val Asn Leu Gly
                85                  90                  95

Arg Phe Pro Ala Ile Trp Asn Gly Phe Leu Ala Ile Phe Ser Ile Leu
            100                 105                 110

Gly Ala Leu Arg Val Val Pro His Phe Leu Phe Leu Phe Thr His Lys
        115                 120                 125

Asp Phe Lys Glu Thr Val Cys Glu Ala Pro Asp Thr Ala Gly Tyr Gly
    130                 135                 140

Asp Gly Ala Ala Gly Met Trp Val Met Leu Phe Thr Val Ser Lys Val
145                 150                 155                 160

Phe Glu Leu Met Asp Thr Val Ile Leu Val Leu Lys Gly Lys Asn Pro
                165                 170                 175

Met Phe Leu His Trp Tyr His His Val Thr Val Leu Leu Tyr Thr Trp
            180                 185                 190

Phe Ser Tyr Ser Ala Arg Asn Pro Gly Leu Tyr Phe Val Ala Met Asn

```
            195                 200                 205
Tyr Thr Val His Ala Val Met Tyr Ser Tyr Tyr Phe Leu Met Glu Ile
    210                 215                 220
Lys Leu Trp Pro Lys Trp Leu Ser Pro Ile Phe Ile Thr Leu Met Gln
225                 230                 235                 240
Ile Ser Gln Met Leu Val Gly Val Gly Ile Thr Ala Ala Ala Tyr Ile
                245                 250                 255
Phe Gln Arg Asp Pro Ser Cys Gly Val Val Arg Asp Leu Ile Pro Trp
            260                 265                 270
Cys Ala Ala Met Tyr Ala Thr Tyr Leu Tyr Phe Phe Val Glu Phe Phe
            275                 280                 285
Val Glu Arg Phe Leu Ala Ala Ser Ser Thr Lys Ala Gly Lys Glu Glu
            290                 295                 300
Gly Lys Gly Gly Lys Ser Gln Leu Ala Lys Lys Asp Ile Gly Thr Ala
305                 310                 315                 320
Ala Phe Ser Leu Val Thr Ala Asn Gly Ala Ser Val Met Gly Asn Gly
                325                 330                 335
Lys Lys Val Val
            340

<210> SEQ ID NO 14
<211> LENGTH: 276
<212> TYPE: PRT
<213> ORGANISM: Nannochloropsis

<400> SEQUENCE: 14

Met Ala Ala Ala Leu Leu Ala Asp Tyr Gln Lys Thr Cys Thr Asp Leu
1               5                   10                  15
Ser Ala Ala Ile Phe Lys Trp Ala Asp Pro Ala Gly Ala Met Val Lys
                20                  25                  30
Ala Pro Thr Arg Thr Trp Pro Leu Ala Gly Leu Asp Val Ala Leu Ala
            35                  40                  45
Ile Ala Ala Phe Tyr Leu Ile Ile Val Phe Val Gly Ser Ala Met Met
    50                  55                  60
Lys Asn Ala Lys Pro Val Lys Leu Tyr Gly Leu Gln Phe Phe Tyr Asn
65                  70                  75                  80
Ile Ser Gln Val Ala Leu Cys Ser Tyr Met Cys Ile Glu Ala Ala Ile
                85                  90                  95
Gln Ala Tyr Arg Asn Asn Tyr Thr Phe Leu Pro Cys Glu Pro Phe Asn
            100                 105                 110
Ala Thr Asn Pro Pro Ile Ala Pro Leu Leu Trp Leu Phe Tyr Val Ser
            115                 120                 125
Lys Val Phe Asp Phe Ala Asp Thr Val Phe Ile Ile Leu Gly Lys Lys
        130                 135                 140
Trp Asn Gln Leu Ser Phe Leu His Val Tyr His Val Thr Ile Phe
145                 150                 155                 160
Leu Val Tyr Trp Leu Asn Leu Asn Ala Gly Tyr Asp Gly Asp Ile Phe
                165                 170                 175
Leu Thr Val Ile Leu Asn Gly Ala Ile His Thr Val Met Tyr Thr Tyr
            180                 185                 190
Tyr Phe Leu Ser Met His Thr Lys Asp Ile Trp Trp Lys Lys Tyr Leu
        195                 200                 205
Thr Leu Phe Gln Ile Ile Gln Phe Leu Thr Met Asn Ala Gln Ala Ile
        210                 215                 220
```

-continued

Tyr Leu Leu Cys Val Gly Cys Lys Gly Phe Ser Pro Gln Ile Thr Lys
225                 230                 235                 240

Leu Tyr Leu Gly Tyr Ile Leu Ser Leu Val Leu Phe Leu Asn Phe
        245                 250                 255

Tyr Phe Lys Ser Tyr Ser Gly Val Lys Pro Asn Gly Lys Lys Pro Val
        260                 265                 270

Ser Lys Lys Ala
        275

<210> SEQ ID NO 15
<211> LENGTH: 241
<212> TYPE: PRT
<213> ORGANISM: Nannochloropsis

<400> SEQUENCE: 15

Met Ile Val Phe Leu Pro Arg Ile Met Lys Asn Arg Pro Val Lys Asp
1               5                   10                  15

Leu Ser Lys Pro Leu Ala Phe Trp Asn Phe Leu Ala Val Tyr Ser
            20                  25                  30

Thr Ile Gly Ala Ile Arg Val Val Pro His Leu Leu Trp Phe Ile Ser
        35                  40                  45

Thr His Thr Phe Lys Glu Thr Val Cys Thr Ala Pro Tyr Arg Ile Asn
    50                  55                  60

Gly Asp Gly Ala Thr Gly Leu Trp Val Thr Leu Phe Thr Leu Ser Lys
65                  70                  75                  80

Val Val Glu Leu Val Asp Thr Leu Phe Ile Cys Leu Lys Gly Lys Lys
                85                  90                  95

Pro Ile Phe Leu His Trp Tyr His Val Ser Val Leu Tyr Phe Thr
            100                 105                 110

Trp Ala Ala His Glu Ala Ala His Ala Gly Met Tyr Phe Ile Gly Met
        115                 120                 125

Asn Tyr Thr Val His Ser Val Met Tyr Ser Tyr Phe Leu Met Ala
    130                 135                 140

Ile Lys Ala Lys Pro Lys Trp Leu Asn Pro Ile Tyr Ile Thr Phe Met
145                 150                 155                 160

Gln Ile Ala Gln Met Ile Val Gly Val Ile Ile Thr Ala Phe Gly Phe
                165                 170                 175

Tyr Tyr Ser Ser Lys Asp Ala Thr Cys Ala Val Asp Pro Phe Val Leu
            180                 185                 190

Lys Ile Ser Gly Val Ile Tyr Ala Ser Tyr Leu Tyr Leu Phe Met Glu
        195                 200                 205

Phe Met Ile Lys Arg Phe Phe Val Gly Gly Gly Val Ala Gly Gly
    210                 215                 220

Lys Lys Lys Gly Gly Ala Ser Pro Arg Lys Ala Lys Ala Lys Lys Ala
225                 230                 235                 240

Leu

<210> SEQ ID NO 16
<211> LENGTH: 224
<212> TYPE: PRT
<213> ORGANISM: Nannochloropsis

<400> SEQUENCE: 16

Met Lys Asn Lys Lys Pro Phe Asp Leu Lys Trp Pro Leu Ala Tyr Trp
1               5                   10                  15

Asn Leu Ala Leu Ser Ile Phe Ser Ile Met Gly Val Ile Arg Val Val

-continued

```
                20                  25                  30
Pro His Leu Val Tyr Leu Thr Ala Thr Lys Gly Leu Ser Val Val Ala
        35                  40                  45

Cys Gly Ala Pro Glu Pro Leu Tyr Gly Asn Ala Ala Val Gly Phe Trp
    50                  55                  60

Val Gln Ala Phe Ile Leu Ser Lys Leu Ala Glu Leu Ile Asp Thr Val
65                  70                  75                  80

Phe Ile Val Leu Arg Lys Lys Pro Leu Gln Phe Leu His Trp Tyr His
                85                  90                  95

His Val Thr Val Leu Leu Phe Thr Trp Phe Cys Tyr Thr Lys Glu Asn
                100                 105                 110

Pro Gly Ile Ile Phe Val Ala Met Asn Tyr Ser Val His Ala Ile Met
            115                 120                 125

Tyr Gly Tyr Tyr Phe Leu Met Ala Ile Gln Val Arg Pro Ser Trp Leu
    130                 135                 140

Lys Pro Ile Tyr Ile Thr Met Met Gln Ile Ser Gln Met Val Val Gly
145                 150                 155                 160

Val Ala Thr Ala Val Phe Tyr Ile Tyr Lys Ile Arg Ser Gly Glu Thr
                165                 170                 175

Cys Ala Val Asp Gln Glu Leu Leu Ile Ala Cys Gly Val Met Tyr Ser
                180                 185                 190

Thr Tyr Leu Tyr Leu Phe Cys Glu Phe Ala Val Lys Arg Phe Ile Leu
            195                 200                 205

Gly Gly Gln Gly Ala Ala Gly Ala Pro Lys Gly Lys Thr Lys Ala Gln
        210                 215                 220
```

ALGAL ELONGASE 6

CROSS-REFERENCE TO RELATED APPLICATIONS

The present application is a continuation of U.S. patent application Ser. No. 13/459,215, filed Apr. 12, 2012, now U.S. Pat. No. 8,809,046, which claims the benefit and priority of U.S. Patent Provisional Application Ser. No. 61/480,364 filed Apr. 28, 2011, titled "Elongases," which is hereby incorporated by reference.

The present application is related to U.S. Non-Provisional patent application Ser. No. 12/581,812 filed on Oct. 19, 2009, titled "Homologous Recombination in an Algal Nuclear Genome," which is hereby incorporated by reference.

The present application is related to U.S. Non-Provisional patent application Ser. No. 12/480,635 filed on Jun. 8, 2009, titled "VCP-Based Vectors for Algal Cell Transformation," which is hereby incorporated by reference.

The present application is related to U.S. Non-Provisional patent application Ser. No. 12/480,611 filed on Jun. 8, 2009, titled "Transformation of Algal Cells," which is hereby incorporated by reference.

REFERENCE TO SEQUENCE LISTINGS

The present application is filed with sequence listing(s) attached hereto and incorporated by reference.

BACKGROUND OF THE INVENTION

Field of the Invention

This invention relates to molecular biology, and more specifically, to algal elongases.

SUMMARY OF THE INVENTION

Isolated nucleotide sequences encoding polypeptides having elongase activity, which utilize fatty acids as substrates.

BRIEF DESCRIPTION OF THE DRAWINGS

FIG. 1 illustrates the nucleotide sequence encoding elongase 1 (SEQ ID NO:1).

FIG. 2 illustrates the nucleotide sequence encoding elongase 2 (SEQ ID NO:2).

FIG. 3 illustrates the nucleotide sequence encoding elongase 3 (SEQ ID NO:3).

FIG. 4 illustrates the nucleotide sequence encoding elongase 4 (SEQ ID NO:4).

FIG. 5 illustrates the nucleotide sequence encoding elongase 5 (SEQ ID NO:5).

FIG. 6 illustrates the nucleotide sequence encoding elongase 6 (SEQ ID NO:6).

FIG. 7 illustrates the nucleotide sequence encoding elongase 7 (SEQ ID NO:7).

FIG. 8 illustrates the nucleotide sequence encoding elongase 8 (SEQ ID NO:8).

FIG. 9 illustrates the amino acid sequence encoding elongase 1 (SEQ ID NO:9).

FIG. 10 illustrates the amino acid sequence encoding elongase 2 (SEQ ID NO:10).

FIG. 11 illustrates the amino acid sequence encoding elongase 3 (SEQ ID NO:11).

FIG. 12 illustrates the amino acid sequence encoded by elongase 4 (SEQ ID NO:12).

FIG. 13 illustrates the amino acid sequence encoded by elongase 5 (SEQ ID NO:13).

FIG. 14 illustrates the amino acid sequence encoded by elongase 6 (SEQ ID NO:14).

FIG. 15 illustrates the amino acid sequence encoded by elongase 7 (SEQ ID NO:15).

FIG. 16 illustrates the amino acid sequence encoded by elongase 8 (SEQ ID NO:16).

DETAILED DESCRIPTION OF THE INVENTION

A fatty acid is a carboxylic acid with a long aliphatic tail (chain), which is either saturated or unsaturated. Saturated fatty acids are long-chain carboxylic acids that usually have between 12 and 24 carbon atoms and have no double bonds. Unsaturated fatty acids have one or more double bonds between carbon atoms. Most naturally occurring fatty acids have a chain of an even number of carbon atoms, from 4 to 28. Elongases are enzymes which lengthen fatty acids by adding two carbon atoms to a fatty acid's carboxylic acid end.

Provided herein are isolated nucleotide sequences encoding polypeptides having elongase activity, which utilize fatty acids as substrates.

The inventors sequenced the entire genome of algal genus *Nannochloropsis* and identified genes involved in fatty acid metabolism. They identified various elongases, including exemplary elongases which they designated as elongases 1-9.

The inventors manipulated the activities of the above-specified exemplary elongase genes by:

1. Overexpression of the subject elongase gene with a strong promoter.

2. Promoter replacement or promoter insertion in front of the subject elongase gene within the genome via homologous recombination.

3. Knock out of the subject elongase gene via insertion of a transformation construct into the gene or replacement of a part of or the entire subject elongase gene via homologous recombination.

Exemplary support for the above-mentioned methods may be found in U.S. Non-Provisional patent application Ser. No. 12/581,812 filed on Oct. 19, 2009, titled "Homologous Recombination in an Algal Nuclear Genome," U.S. Non-Provisional patent application Ser. No. 12/480,635 filed on Jun. 8, 2009, titled "VCP-Based Vectors for Algal Cell Transformation," and U.S. Non-Provisional patent application Ser. No. 12/480,611 filed on Jun. 8, 2009, titled "Transformation of Algal Cells," all of which are hereby incorporated by reference.

Accordingly, the inventors were able to manipulate the activities of the various exemplary elongases for the purpose of modifying the contents of certain fatty acids within algal genus *Nannochloropsis*.

Some of these elongases, i.e. Elongases 6-8, are down-regulated under conditions when poly unsaturated fatty acid ("PUFA") biosynthesis is down-regulated as well (i.e. during Nitrogen starvation). These genes are excellent targets for over-expression, in order to achieve elevated PUFA biosynthesis. Down-regulation of these (or other) genes, as an example, by replacement of the endogenous promoter or insertion of a weaker promoter in front of the respective elongase gene could lead to a higher content of short chain fatty acids. Down-regulation of transcription could also be achieved, in some cases, by insertion of a commonly strong promoter in front of the respective elongase gene, presumably by modifying the respective chromatin arrangement around the said elongase gene, thus leading to a lower transcription level. Also, the introduction of point mutations into the gene when inserting another promoter in front of such a gene via the homologous recombination flanks utilized, could lead to an altered activity of the respective gene products.

Over expression and knock out mutants of said elongase genes suggest that at least 4 elongases with overlapping functions are operating in the biosynthesis pathway leading to Eicosapentaenoic acid ("EPA"): these are, but not limited to: Elongases 5, 6, 7, and 9. Transcriptome analysis also suggests that Elongase 8 is operating as well in the fatty acid biosynthesis pathway to EPA.

FIG. 1 illustrates the nucleotide sequence encoding elongase 1 (SEQ ID NO:1).

FIG. 2 illustrates the nucleotide sequence encoding elongase 2 (SEQ ID NO:2).

FIG. 3 illustrates the nucleotide sequence encoding elongase 3 (SEQ ID NO:3).

FIG. 4 illustrates the nucleotide sequence encoding elongase 4 (SEQ ID NO:4).

FIG. 5 illustrates the nucleotide sequence encoding elongase 5 (SEQ ID NO:5).

FIG. 6 illustrates the nucleotide sequence encoding elongase 6 (SEQ ID NO:6).

FIG. 7 illustrates the nucleotide sequence encoding elongase 7 (SEQ ID NO:7).

FIG. 8 illustrates the nucleotide sequence encoding elongase 8 (SEQ ID NO:8).

FIG. 9 illustrates the amino acid sequence encoding elongase 1 (SEQ ID NO:9).

FIG. 10 illustrates the amino acid sequence encoding elongase 2 (SEQ ID NO:10).

FIG. 11 illustrates the amino acid sequence encoding elongase 3 (SEQ ID NO:11).

FIG. 12 illustrates the amino acid sequence encoded by elongase 4 (SEQ ID NO:12).

FIG. 13 illustrates the amino acid sequence encoded by elongase 5 (SEQ ID NO:13).

FIG. 14 illustrates the amino acid sequence encoded by elongase 6 (SEQ ID NO:14).

FIG. 15 illustrates the amino acid sequence encoded by elongase 7 (SEQ ID NO:15).

FIG. 16 illustrates the amino acid sequence encoded by elongase 8 (SEQ ID NO:16).

While various embodiments have been described above, it should be understood that they have been presented by way of example only, and not limitation. Thus, the breadth and scope of a preferred embodiment should not be limited by any of the above-described exemplary embodiments.

What is claimed is:

1. A method of modulating poly unsaturated fatty acid biosynthesis in an algal cell, said method comprising:
enhancing or suppressing expression of an elongase 6 comprising the amino acid sequence of SEQ ID NO: 14 in said algal cell,
wherein said enhancing expression comprises replacement of an endogenous promoter with a strong promoter in front of a gene encoding said elongase 6,
wherein said suppressing expression is selected from the group consisting of replacement of an endogenous promoter with a weak promoter in front of a gene encoding said elongase 6, an insertion in a gene encoding said elongase 6 comprising the amino acid sequence of SEQ ID NO: 14, and a deletion or a substitution of a portion or a full length of said gene encoding elongase 6 comprising the amino acid sequence of SEQ ID NO: 14,
wherein said strong promoter is stronger than said endogenous promoter and said weak promoter is weaker than said endogenous promoter;
thereby modulating poly unsaturated fatty acid biosynthesis in said algal cell.

2. The method of claim 1, wherein said expression of said elongase 6 is enhanced and eicosapentaenoic acid (EPA) production is increased in said algal cell relative to an algal cell without said enhanced expression.

3. The method of claim 1, wherein said expression of said elongase 6 is suppressed and EPA production is decreased in said algal cell relative to an algal cell without said suppressed expression.

4. The method of claim 1, wherein said algal cell is a *Nannochloropsis* cell.

5. The method of claim 1, wherein said algal cell comprises an insertion in said gene encoding said elongase 6 comprising the amino acid sequence of SEQ ID NO: 14.

6. The method of claim 1, wherein said algal cell comprises a deletion or a substitution of a portion or a full length of said gene encoding elongase 6 comprising the amino acid sequence of SEQ ID NO: 14.

* * * * *